United States Patent
Dodge et al.

(10) Patent No.: US 6,509,356 B1
(45) Date of Patent: Jan. 21, 2003

(54) 1-(4-(SUBSTITUTED ALKOXY)BENZYL) NAPHTHALENE COMPOUNDS HAVING ESTROGEN INHIBITORY ACTIVITY

(75) Inventors: Jeffrey Alan Dodge, Indianapolis, IN (US); Andrew Lawrence Glasebrook, Zionsville, IN (US); Charles Willis Lugar, III, McCordsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/129,119

(22) Filed: Aug. 4, 1998

Related U.S. Application Data

(60) Provisional application No. 60/054,952, filed on Aug. 7, 1997.

(51) Int. Cl.[7] .................... A61K 31/445; C07D 211/06
(52) U.S. Cl. .................. 514/319; 514/213; 514/331; 514/428; 514/650; 540/585; 540/609; 544/105; 546/192; 546/205; 546/229; 546/233; 548/566; 548/570; 548/571; 548/575
(58) Field of Search ................ 546/205, 192, 546/229, 233; 514/213, 319, 331, 428, 650; 540/585, 609; 544/105; 548/566, 570, 571, 575

(56) References Cited

U.S. PATENT DOCUMENTS

| | | | |
|---|---|---|---|
| 2,703,324 A | 3/1955 | Binkley et al. | 548/353.1 |
| 3,274,213 A | 9/1966 | Lednicer | 546/205 |
| 3,394,125 A | 7/1968 | Crenshaw | 548/525 |
| 3,396,169 A | 8/1968 | Lednicer | 546/205 |
| 3,413,305 A | 11/1968 | Crenshaw | 548/525 |
| 4,133,814 A | 1/1979 | Jones et al. | 546/202 |
| 4,230,862 A | 10/1980 | Suarez et al. | 546/237 |
| 4,358,593 A | 11/1982 | Jones et al. | 546/202 |
| 4,380,635 A | 4/1983 | Peters | 546/202 |
| 4,418,068 A | 11/1983 | Jones | 546/237 |
| 4,732,896 A | 3/1988 | Bourgery et al. | 514/212 |
| 5,395,842 A | 3/1995 | Labrie | 514/320 |
| 5,470,854 A | 11/1995 | von Angerer et al. | 514/233 |
| 5,472,962 A | 12/1995 | Koizumi et al. | 514/233.5 |
| 5,484,795 A | 1/1996 | Bryant et al. | 514/319 |
| 5,484,797 A | 1/1996 | Bryant et al. | 514/238.8 |
| 5,510,357 A | 4/1996 | Palkowitz | 514/324 |
| 5,541,228 A | 7/1996 | Takaki et al. | 514/630 |
| 5,552,412 A | 9/1996 | Cameron et al. | 514/317 |
| 5,554,628 A * | 9/1996 | Bryant et al. | 514/319 |
| 5,567,712 A | 10/1996 | Palkowitz | 514/231.2 |
| 5,574,190 A | 11/1996 | Palkowitz | 568/440 |
| 5,658,931 A * | 8/1997 | Bryant et al. | 514/319 |

FOREIGN PATENT DOCUMENTS

| | | |
|---|---|---|
| EP | 062 503 | 10/1982 |
| EP | 0 124 369 | 4/1984 |
| EP | 0 702 961 | 9/1994 |
| EP | 0 702 962 | 9/1994 |
| EP | 0 703228 | 9/1994 |
| EP | 702962 * | 3/1996 |
| GB | 2 312 844 | 5/1996 |
| WO | WO 89/02893 | 4/1989 |
| WO | WO 95/10513 | 4/1995 |
| WO | WO 97/04763 | 7/1995 |

OTHER PUBLICATIONS

Caignard "Structural activity relation ships of . . . " CA 126:70291 (1994).*

Roark et al. "Inhibitors of acy–coA:cholesterl . . . " CA 119:49034 (1993).*

Crenshaw, R.R., et al., Potential Antifertility Agents, *J. Med. Chem.* vol. 14, No. 12, pp. 1185–1190 (1971).

Jones, C.D., et al., Antiestrogens, *J. Med. Chem.* vol. 27, pp. 1057–1066 (1984).

Jones, C.D., et al., Antiestrogens, *J. Med. Chem.* vol. 35, pp. 931–938 (1992).

(List continued on next page.)

*Primary Examiner*—Ceila Chang
(74) *Attorney, Agent, or Firm*—Gary M. Birch; Gilbert T. Voy; James J. Sales

(57) ABSTRACT

A class of substituted benzylnaphthylene compounds of the structure

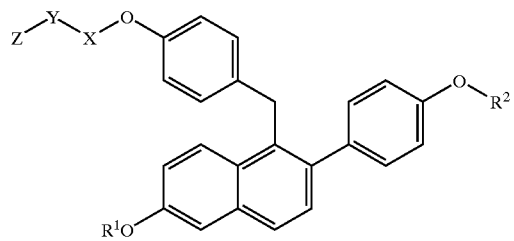

where $R^1$ and $R^2$ are independently hydrogen, alkyl of one to six carbon atoms, acyl of two to six carbon atoms, or phenacyl; X is —$(CH_2)_{1-6}$; Y is absent or is selected from 1,4-piperazinylene; ureido; N-(lower alkyl)ureido; N'-(lower alkyl)ureido; or N, N'-(di-lower alkyl ureido; and Z is 1-, 2- or 3-pyrrolidinyl; 1-, 2-, or 3-[1-(lower alkyl)pyrrolidinyl]; 1- 2-, 3- or 4-piperidinyl; 1-, 2-, 3- or 4-[1-lower alkyl)piperidinyl]; N,N-dialkyl; 1-azepinyl; 1- or 2-naphthylamino, 4-morpholinyl, dimethyl-4-morpholinyl, 3-azaspiro[5.5]undecan-3-yl; pyrrolidinon-1-yl; unsubstituted phenyl; or phenyl substituted with acyl of two to four carbon atoms, alkyl of one to four carbon atoms, halo, or alkoxy of one to four carbon atoms; with the proviso that n is not 2 or 3 when Z is 1-pyrrolidinyl, 1-piperidinyl, 1-azepinyl, 4-morpholinyl, N,N-dimethylamino or N,N-diethylamino; are selective estrogen receptor modulators useful in the prophylaxis or treatment of breast cancer.

17 Claims, No Drawings

OTHER PUBLICATIONS

Grease, T.A., et al., Structure–Activity Relationships of Selective Estrogen Receptor Modulators, *J. Med. Chem.* vol. 40, No. 2 pp. 146–167.

Kauffman, R.F., et al., Hypocholesterolemic Activity of Raloxifene (LY139481) Pharmacological Characterization as a Selective Estrogen Receptor Modulator, *J. Phar. And Experimental Therapeutics*, vol. 280, No. 1, pp. 146–153 (1997).

Lantz, M.D., et al., Simultaneous Resolution and Detection of A Drug Substance, Impurities, and Counter Ion Using A Mixed–Mode HPLC Column with Evaporative Light Scattering Detection, J–LIQ. *Chrom. & Rel. Technol.*, vol. 20, No. 9, pp. 1409–1422 (1997).

Collins, et al., Antioestrogenic and Antiferility Conpounds. *Aust. J. Chem.*, vol. 20 pp. 1413–1428, especially p. 1415 (1967).

\* cited by examiner

1-(4-(SUBSTITUTED ALKOXY)BENZYL) NAPHTHALENE COMPOUNDS HAVING ESTROGEN INHIBITORY ACTIVITY

This Application claims the benefit of U.S. Provisional Application No. 60/054,952, filed Aug. 7, 1997.

TECHNICAL FIELD

The present invention relates to organic compounds having pharmacological activity, to compositions containing the compounds, and to a medical method of treatment.

More particularly, the present invention concerns a class of 1-[4-(substituted alkoxy)benzyl]naphthalene compounds having estrogenic activity; to pharmaceutical compositions containing the compounds and to a method of treating or inhibiting cancer of the breast or uterus.

BACKGROUND OF THE INVENTION

Estrogen is a generic term for estrus-producing steroid compounds. Within the "estrogen group" are the traditional steroids such as 17β-estradiol and estrone (the major estrogens in humans), as well as various metabolites such as the estratriols, sulfates and glucuronides of estradiol and estrone. Also, germane to human medicine, are the steroidal equine estrogens such as the equilins, in that they are administered to humans in preparations, such as Premarin™. Also, certain compounds known as "anti-estrogens", e.g., tamoxifen, clomiphene, and nafoxidene, demonstrate varying degrees of estrogen agonist properties in some tissues; however they act to antagonize the natural estrogens and their function in other tissues.

Recently, these "anti-estrogens" have been categorized into three different types depending on their degree and mix of estrogen agonist/antagonist properties which is based on their ability to freeze estrogen receptors in different conformational states, cf. D. P. McDonnell, et al., *Molecular Endocrinology*, 9(6): 659–669 (1995). Most germane are the type II anti-estrogens of which compounds of the current invention belong.

Estrogens as biologically active molecules exert their properties by binding to an intracellular receptor. After the receptor and bound ligand are transported to the nucleus of a cell, the complex exerts its effect by binding to certain recognition sites on DNA and allowing certain genes to be expressed. This binding to the receptor and regulation is not completely understood at this time; however, it appears to be crucial to the varying degree of agonistic and antagonistic properties of a molecule. Thus, certain types of so-called "anti-estrogens" allow agonist activity in some tissues, but are antagonists in others. Hence, the term, "selective estrogen receptor modulators (SERMs)" has been proposed to describe these molecules, especially the type II, of which the compounds of the present invention are members.

Estrogen has long been classified as "the female sex hormone" and a voluminous literature describes its activity as such. However, in recent years, research has shown that estrogens have many other homeostatic functions, other than those related to female reproduction and function of sex tissues. Indeed, it has been shown that males possess estrogen receptors and DNA recognition sites and possess the ability to produce estrogens and many tissues, such as those involved in the cardiovascular system. The exact nature of the effects of estrogens in both men and women, outside the productive aspects, are only beginning to be explored and are currently poorly understood.

The majority of the documented activities of the estrogens have been derived from studies in women, since most women suffer from the most obvious effects of estrogen, mainly due to menopause and estrogen dependent cancers. The clinical pathologies associated with estrogen levels and their subsequent function, can be categorized into two main types, i.e., those which are due to a deprivation or lack of estrogen and those which are due to an aberrant physiological response to existing estrogen in estrogen sensitive tissues. SERMS, especially those of type II, have the property of being estrogen agonists in those cases where estrogen deprivation is a cause of pathology (mainly in non-sex related tissues) and simultaneously being antagonists of the pathologies caused by abnormal responses to endogenous estrogen (in sex related tissues).

Thus, SERMS of the type II have the potential to effectively treat a variety of estrogen dependent pathological conditions. This dual effect is an intrinsic and unique property of the molecules of the present invention.

SUMMARY OF THE INVENTION

In its principal embodiment, the present invention provides a selective estrogen modulating compound of structure 1:

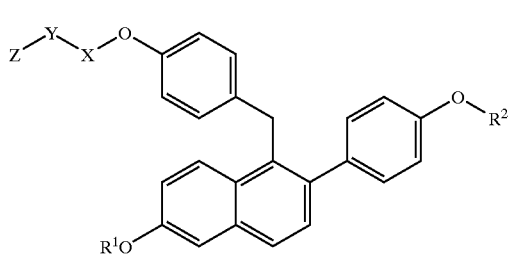

or a pharmaceutically acceptable salt thereof where $R^1$ and $R^2$ are independently selected from hydrogen, alkyl of one to six carbon atoms, acyl of two to six carbon atoms, and phenacyl.

The group designated X is —$(CH_2)_n$ where n is an integer of one to 6, inclusive.

Y is absent or is selected from the group consisting of 1,4-piperazinylene; ureido; N-(lower alkyl)ureido; N'-(lower alkyl)ureido; and N,N'-(di-lower alkyl ureido.

The substitutent Z is selected from the group consisting of 1-, 2- or 3-pyrrolidinyl; 1-, 2-, or 3-[1-(lower alkyl) pyrrolidinyl]; 1- 2-, 3- or 4-piperidinyl; 1-, 2-, 3- or 4-[1-lower alkyl)piperidinyl]; N,N-dialkyl in which the alkyl groups are independently from one to four carbon atoms; 1-azepinyl; 1- or 2-naphthylamino; 4-morpholinyl; dimethyl-4-morpholinyl; 3-azaspiro[5.5]undecan-3-yl; pyrrolidinon-1-yl; unsubstituted phenyl; and phenyl substituted with one or two groups independently selected from acyl of two to four carbon atoms, alkyl of one to four carbon atoms, halo, and alkoxy of one to four carbon atoms.

All of the above definitions are with the proviso that n is not 2 or 3 when Z is 1-pyrrolidinyl, 1-piperidinyl, 1-azepinyl, 4-morpholinyl, N,N-dimethylamino or N,N-diethyl-amino.

In a second embodiment, the present invention provides pharmaceutical compositions comprising a therapeutically effective amount of a compound as defined above in combination with a pharmaceutically acceptable carrier.

In another embodiment, the present invention comprises a method of treating or inhibiting estrogen-dependent cancers in women, particularly cancer of the breast and uterus, comprising administering to a woman in need of such treatment an effective amount of a compound as defined above.

DETAILED DESCRIPTION

As used throughout this specification and the appended claims, the following terms have the meanings ascribed to them.

"Alkyl of one to six carbon atoms" means a univalent radical derived by the removal of one hydrogen atom from methane, ethane, or a straight or branched hydrocarbon of three to six carbon atoms and is typified by methyl, ethyl, n- or iso-propyl, n-, sec- iso- or tert-butyl, n-pentyl, 2-methylbutyl, n-hexyl, 2-methylpentyl, 2,3-dimethylbutyl, and the like.

"Acyl" denotes an alkyl group as defined above, attached to the parent molecular moiety through a carbonyl group.

"Lower alkyl" denotes an alkyl group as defined above containing one to four carbon atoms.

The term "alkoxy" refers to an alkyl group, as defined above, attached to the parent molecular moiety through an oxygen atom.

The term "1,4-piperazinylene" denotes a divalent radical of the structure:

and the term "ureido" means the divalent radical represented by the structure

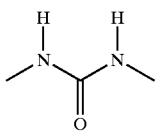

The term "N-(lower alkyl)ureido", as used herein, means a ureido group in which the lower alkyl group is attached to the nitrogen nearest the group denoted "X" in structure 1 above, thus:

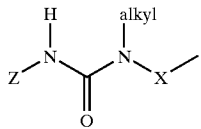

and "N'-(lower alkyl)ureido" means a ureido group in which the lower alkyl group is attached to the nitrogen nearest the group denoted "Z" in structure I above, thus:

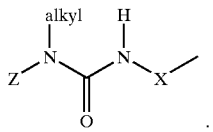

Compounds contemplated as falling within the scope of the present invention include, but are not limited to, the following representative examples.

Compounds of the present invention in which Y is absent, and Z is alkyl or dialkyl include:

6-hydroxy-2-(4-hydroxyphenyl)-1-[4-(N-methylamino) methoxy-benzyl]naphthalene;
6-hydroxy-2-(4-hydroxyphenyl)-1-[4-(N,N-dimethylamino)-methoxybenzyl]naphthalene;
6-hydroxy-2-(4-hydroxyphenyl)-1-[4-(N-isopropylamino)-methoxybenzyl]naphthalene;
6-hydroxy-2-(4-hydroxyphenyl)-1-[4-(N,N-diisopropylamino)-methoxybenzyl]naphthalene;
6-hydroxy-2-(4-hydroxyphenyl)-1-[4-(2-(N-isopropylamino)-ethoxy)benzyl]naphthalene;
6-hydroxy-2-(4-hydroxyphenyl)-1-[4-(3-(N-isopropylamino)-propoxy)benzyl]naphthalene;
6-hydroxy-2-(4-hydroxyphenyl)-1-[4-(3-(N,N-diisopropylamino)propoxy)benzyl]naphthalene;
6-hydroxy-2-(4-hydroxyphenyl)-1-[4-(3-(N-butylamino)-propoxy)benzyl]naphthalene;
6-hydroxy-2-(4-hydroxyphenyl)-1-[4-(3-(N,N-dibutylamino)-propoxy)benzyl]naphthalene;
6-hydroxy-2-(4-hydroxyphenyl)-1-[4-(6-(N-methylamino)-hexoxy)benzyl]naphthalene;
6-hydroxy-2-(4-hydroxyphenyl)-1-[4-(6-(N,N-dimethylamino)-hexoxy)benzyl]naphthalene;
6-hydroxy-2-(4-hydroxyphenyl)-1-[4-(6-(N-ethylamino)-hexoxy)benzyl]naphthalene;
6-hydroxy-2-(4-hydroxyphenyl)-1-[4-(6-(N,N-diethylamino)-hexoxy)benzyl]naphthalene;
6-hydroxy-2-(4-hydroxyphenyl)-1-[4-(6-(N-isopropylamino)-hexoxy)benzyl]naphthalene;
6-hydroxy-2-(4-hydroxyphenyl)-1-[4-(6-(N,N-diisopropylamino)hexoxy)benzyl]naphthalene;
6-hydroxy-2-(4-hydroxyphenyl)-1-[4-(6-(N-butylylamino)-hexoxy)benzyl]naphthalene; and
6-hydroxy-2-(4-hydroxyphenyl)-1-[4-(6-(N,N-dibutylamino)-hexoxy)benzyl]naphthalene.

Examples of compounds of the present invention in which X is alkylene, Y is absent, and Z is pyrrolidinyl include:

6-hydroxy-2-(4-hydroxyphenyl)-1-[4-(pyrrolidin-1-yl) methoxy-benzyl]naphthalene;
6-hydroxy-2-(4-hydroxyphenyl)-1-[4-(pyrrolidin-2-yl) methoxy-benzyl]naphthalene;
6-hydroxy-2-(4-hydroxyphenyl)-1-[4-(pyrrolidin-3-yl) methoxy-benzyl]naphthalene;
6-hydroxy-2-(4-hydroxyphenyl)-1-[4-(2-(pyrrolidin-2-yl)-ethoxy)benzyl]naphthalene;
6-hydroxy-2-(4-hydroxyphenyl)-1-[4-(2-(pyrrolidin-3-yl)-ethoxy)benzyl]naphthalene;
6-hydroxy-2-(4-hydroxyphenyl)-1-[4-(3-(pyrrolidin-2-yl)-propoxy)benzyl]naphthalene;
6-hydroxy-2-(4-hydroxyphenyl)-1-[4-(3-(pyrrolidin-3-yl)-propoxy)benzyl]naphthalene;
6-hydroxy-2-(4-hydroxyphenyl)-1-[4-(4-(pyrrolidin-1-yl)-butoxy)benzyl]naphthalene;
6-hydroxy-2-(4-hydroxyphenyl)-1-[4-(4-(pyrrolidin-2-yl)-butoxy)benzyl]naphthalene; and
6-hydroxy-2-(4-hydroxyphenyl)-1-[4-(4-(pyrrolidin-3-yl)-butoxy)benzyl]naphthalene.

Compounds of the present invention in which Y is absent, and Z is pyrrolidinon-1-yl include:

6-hydroxy-2-(4-hydroxyphenyl)-1-[4-(pyrrolidinon-1-yl)-methoxybenzyl]naphthalene;
6-hydroxy-2-(4-hydroxyphenyl)-1-[4-(2-(pyrrolidinon-1-yl)-ethoxy)benzyl]naphthalene;
6-hydroxy-2-(4-hydroxyphenyl)-1-[4-(3-(pyrrolidinon-1-yl)-propoxy)benzyl]naphthalene; and
6-hydroxy-2-(4-hydroxyphenyl)-1-[4-(4-(pyrrolidinon-1-yl)-butoxy)benzyl]naphthalene.

Compounds of the present invention in which Y is absent, and Z is piperidinyl include:

6-hydroxy-2-(4-hydroxyphenyl)-1-[4-(piperidin-1-yl)-methoxybenzyl]naphthalene;
6-hydroxy-2-(4-hydroxyphenyl)-1-[4-(piperidin-2-yl)-methoxybenzyl]naphthalene;
6-hydroxy-2-(4-hydroxyphenyl)-1-[4-(N-methylpiperidin-2-yl)-methoxybenzyl]naphthalene;
6-hydroxy-2-(4-hydroxyphenyl)-1-[4-(piperidin-3-yl)-methoxybenzyl]naphthalene;
6-hydroxy-2-(4-hydroxyphenyl)-1-[4-(N-methylpiperidin-3-yl)-methoxybenzyl]naphthalene;
6-hydroxy-2-(4-hydroxyphenyl)-1-[4-(piperidin-4-yl)-methoxybenzyl]naphthalene;
6-hydroxy-2-(4-hydroxyphenyl)-1-[4-(2-(piperidin-2-yl)-ethoxy)benzyl]naphthalene;
6-hydroxy-2-(4-hydroxyphenyl)-1-[4-(2-(piperidin-3-yl)-ethoxy)benzyl]naphthalene;
6-hydroxy-2-(4-hydroxyphenyl)-1-[4-(2-(piperidin-4-yl)-ethoxy)benzyl]naphthalene;
6-hydroxy-2-(4-hydroxyphenyl)-1-[4-(3-(piperidin-2-yl)-propoxy)benzyl]naphthalene;
6-hydroxy-2-(4-hydroxyphenyl)-1-[4-(3-(piperidin-3-yl)-propoxy)benzyl]naphthalene;
6-hydroxy-2-(4-hydroxyphenyl)-1-[4-(3-(piperidin-4-yl)-propoxy)benzyl]naphthalene;
6-hydroxy-2-(4-hydroxyphenyl)-1-[4-(4-(piperidin-1-yl)-butoxy)benzyl]naphthalene;
6-hydroxy-2-(4-hydroxyphenyl)-1-[4-(4-(piperidin-2-yl)-butoxy)benzyl]naphthalene;
6-hydroxy-2-(4-hydroxyphenyl)-1-[4-(4-(piperidin-3-yl)-butoxy)benzyl]naphthalene; and
6-hydroxy-2-(4-hydroxyphenyl)-1-[4-(4-(piperidin-4-yl)-butoxy)benzyl]naphthalene.

Compounds of the present invention in which Y is absent and Z is azepinyl include:

6-hydroxy-2-(4-hydroxyphenyl)-1-[4-(azepin-1-yl)methoxy-benzyl]naphthalene;
6-hydroxy-2-(4-hydroxyphenyl)-1-[4-(azepin-2-yl)methoxy-benzyl]naphthalene;
6-hydroxy-2-(4-hydroxyphenyl)-1-[4-(azepin-3-yl)methoxy-benzyl]naphthalene;
6-hydroxy-2-(4-hydroxyphenyl)-1-[4-(azepin-4-yl)methoxy-benzyl]naphthalene;
6-hydroxy-2-(4-hydroxyphenyl)-1-[4-(2-(azepin-2-yl)-ethoxy)benzyl]naphthalene;
6-hydroxy-2-(4-hydroxyphenyl)-1-[4-(2-(azepin-3-yl)-ethoxy)benzyl]naphthalene;
6-hydroxy-2-(4-hydroxyphenyl)-1-[4-(3-(azepin-2-yl)-propoxy)benzyl]naphthalene;
6-hydroxy-2-(4-hydroxyphenyl)-1-[4-(3-(azepin-3-yl)-propoxy)benzyl]naphthalene;
6-hydroxy-2-(4-hydroxyphenyl)-1-[4-(4-(azepin-1-yl)-butoxy)benzyl]naphthalene;
6-hydroxy-2-(4-hydroxyphenyl)-1-[4-(4-(azepin-2-yl)-butoxy)benzyl]naphthalene;
6-hydroxy-2-(4-hydroxyphenyl)-1-[4-(4-(azepin-3-yl)-butoxy)benzyl]naphthalene; and
6-hydroxy-2-(4-hydroxyphenyl)-1-[4-(4-(azepin-4-yl)-butoxy)benzyl]naphthalene.

Compounds of the present invention in which Y is absent and Z is 4-morpholinyl include:

6-hydroxy-2-(4-hydroxyphenyl)-1-[4-(morpholin-4-yl-methoxy)benzyl]naphthalene;
6-hydroxy-2-(4-hydroxyphenyl)-1-[(4-(4-(morpholin-4-yl)-butoxy)benzyl]naphthalene;
6-hydroxy-2-(4-hydroxyphenyl)-1-[4-(5-(morpholin-4-yl)-heptoxy)benzyl]naphthalene;
6-hydroxy-2-(4-hydroxyphenyl)-1-[4-(6-(morpholin-4-yl)hexoxy)benzyl]naphthalene;
6-hydroxy-2-(4-hydroxyphenyl)-1-[4-(2,6-dimethylmorpholin-4-ylmethoxy)benzyl]naphthalene;
6-hydroxy-2-(4-hydroxyphenyl)-1-[4-(2-(2,6-dimethyl-morpholin-4-yl)ethoxy)benzyl]naphthalene; and
6-hydroxy-2-(4-hydroxyphenyl)-1-[4-(3-(2,6-dimethyl-morpholin-4-yl)propoxy)benzyl]naphthalene.

Compounds of the present invention in which Y is absent and Z is 1- or 2-aminonaphthyl include:

6-hydroxy-2-(4-hydroxyphenyl)-1-[4-(naphth-1-ylamino)-methoxy)benzyl]naphthalene;
6-hydroxy-2-(4-hydroxyphenyl)-1-[4-(2-(naphth-1-ylamino)-ethoxy)benzyl]naphthalene;
6-hydroxy-2-(4-hydroxyphenyl)-1-[4-(3-(naphth-1-ylamino)-propoxy)benzyl]naphthalene;
6-hydroxy-2-(4-hydroxyphenyl)-1-[4-(4-(naphth-1-ylamino)-butoxy)benzyl]naphthalene;
6-hydroxy-2-(4-hydroxyphenyl)-1-[4-(naphth-2-ylamino)-methoxybenzyl]naphthalene;
6-hydroxy-2-(4-hydroxyphenyl)-1-[4-(2-(naphth-2-ylamino)-ethoxy)benzyl]naphthalene;
6-hydroxy-2-(4-hydroxyphenyl)-1-[4-(3-(naphth-2-ylamino)-propoxy)benzyl]naphthalene; and
6-hydroxy-2-(4-hydroxyphenyl)-1-[4-(4-(naphth-2-ylamino)-butoxy)benzyl]naphthalene.

Compounds of the present invention in which Y is absent and Z is 3-azaspiro[5.5]undec-3-yl include:

6-hydroxy-2-(4-hydroxyphenyl)-1-[4-(3-azaspiro[5.5]undec-3-yl)methoxybenzyl]naphthalene;
6-hydroxy-2-(4-hydroxyphenyl)-1-[4-(2-(3-azaspiro[5.5]undec-3-yl)ethoxy)benzyl]naphthalene;
6-hydroxy-2-(4-hydroxyphenyl)-1-[4-(3-(3-azaspiro[5.5]undec-3-yl)propoxy)benzyl]naphthalene; and
6-hydroxy-2-(4-hydroxyphenyl)-1-[4-(4-(3-azaspiro[5.5]undec-3-yl)butoxy)benzyl]naphthalene.

Compounds of the present invention in which Y is absent and Z is 2,3,5,6-tetrahydro-2,6-dioxo-1,3-dimethyl-1H-purin-8-yl include:

6-hydroxy-2-(4-hydroxyphenyl)-1-[4-(2,3,5,6-tetrahydro-2,6-dioxo-1,3-dimethyl-1H-purin-8-yl)methoxybenzyl]-naphthalene;
6-hydroxy-2-(4-hydroxyphenyl)-1-[4-(2-(2,3,5,6-tetrahydro-2,6-dioxo-1,3-dimethyl-1H-purin-8-yl)ethoxy)benzyl]-naphthalene;
6-hydroxy-2-(4-hydroxyphenyl)-1-[4-(3-(2,3,5,6-tetrahydro-2,6-dioxo-1,3-dimethyl-1H-purin-8-yl)propoxy)benzyl]-naphthalene; and
6-hydroxy-2-(4-hydroxyphenyl)-1-[4-(4-(2,3,5,6-tetrahydro-2,6-dioxo-1,3-dimethyl-1H-purin-8-yl)butoxy)benzyl]-naphthalene.

Compounds of the present invention in which Y is 1,4-piperazinylene and Z is phenyl or substituted phenyl include:

6-hydroxy-2-(4-hydroxyphenyl)-1-[4-(4-phenylpiperazin-1-ylmethoxy)benzyl]naphthalene;
6-hydroxy-2-(4-hydroxyphenyl)-1-[4-(2-(4-phenylpiperazin-1-yl)ethoxy)benzyl]naphthalene;
6-hydroxy-2-(4-hydroxyphenyl)-1-[4-(3-(4-phenylpiperazin-1-yl)propoxy)benzyl]naphthalene;
6-hydroxy-2-(4-hydroxyphenyl)-1-[4-(4-(4-phenylpiperazin-1-yl)butoxy)benzyl]naphthalene;
6-hydroxy-2-(4-hydroxyphenyl)-1-[4-(4-(4-methylphenyl)-piperazin-1-ylmethoxy)benzyl]naphthalene;
6-hydroxy-2-(4-hydroxyphenyl)-1-[4-(4-(4-chlorophenyl)-piperazin-1-ylmethoxy)benzyl]naphthalene;
6-hydroxy-2-(4-hydroxyphenyl)-1-[4-(4-(4-hydroxyphenyl)-piperazin-1-ylmethoxy)benzyl]naphthalene;
6-hydroxy-2-(4-hydroxyphenyl)-1-[4-(4-(4-methoxyphenyl)-piperazin-1-ylmethoxy)benzyl]naphthalene;
6-hydroxy-2-(4-hydroxyphenyl)-1-[4-(4-(4-acetylphenyl)-piperazin-1-ylmethoxy)benzyl]naphthalene;
6-hydroxy-2-(4-hydroxyphenyl)-1-[4-(2-(4-(4-methylphenyl)-piperazin-1-yl)ethoxy)benzyl]naphthalene;
6-hydroxy-2-(4-hydroxyphenyl)-1-[4-(2-(4-(4-chlorophenyl)-piperazin-1-yl)ethoxy)benzyl]naphthalene;
6-hydroxy-2-(4-hydroxyphenyl)-1-[4-(2-(4-(4-hydroxyphenyl)-piperazin-1-yl)ethoxy)benzyl]naphthalene;
6-hydroxy-2-(4-hydroxyphenyl)-1-[4-(2-(4-(4-methoxyphenyl)-piperazin-1-yl)ethoxy)benzyl]naphthalene;
6-hydroxy-2-(4-hydroxyphenyl)-1-[4-(2-(4-(4-acetylphenyl)-piperazin-1-yl)ethoxy)benzyl]naphthalene;
6-hydroxy-2-(4-hydroxyphenyl)-1-[4-(3-(4-(4-methylphenyl)-piperazin-1-yl)propoxy)benzyl]naphthalene;
6-hydroxy-2-(4-hydroxyphenyl)-1-[4-(3-(4-(4-chlorophenyl)-piperazin-1-yl)propoxy)benzyl]naphthalene;
6-hydroxy-2-(4-hydroxyphenyl)-1-[4-(3-(4-(4-hydroxyphenyl)-piperazin-1-yl)propoxy)benzyl]naphthalene;
6-hydroxy-2-(4-hydroxyphenyl)-1-[4-(3-(4-(4-methoxyphenyl)-piperazin-1-yl)propoxy)benzyl]naphthalene; and
6-hydroxy-2-(4-hydroxyphenyl)-1-[4-(3-(4-(4-acetylphenyl)-piperazin-1-yl)propoxy)benzyl]naphthalene.

Compounds of the present invention in which Y is ureido and Z is phenyl or substituted phenyl include:

N-[4-(6-hydroxy-2-(4-hydroxyphenyl)naphth-1-ylmethyl)-phenylmethyl]-N'-phenyl urea;
N-[4-(2-(6-hydroxy-2-(4-hydroxyphenyl)naphth-1-ylmethyl)-phenyl)ethyl]-N'-phenyl urea;
N-[4-(3-(6-hydroxy-2-(4-hydroxyphenyl)naphth-1-ylmethyl)-phenylpropyl]-N'-phenyl urea;
N-[4-(6-hydroxy-2-(4-hydroxyphenyl)naphth-1-ylmethyl)-phenylmethyl]-N'-4-methylphenyl urea;
N-[4-(6-hydroxy-2-(4-hydroxyphenyl)naphth-1-ylmethyl)-phenylmethyl]-N'-4-chlorophenyl urea;
N-[4-(6-hydroxy-2-(4-hydroxyphenyl)naphth-1-ylmethyl)-phenylmethyl]-N'-4-hydroxyphenyl urea;
N-[4-(6-hydroxy-2-(4-hydroxyphenyl)naphth-1-ylmethyl)-phenylmethyl]-N'-4-methoxyphenyl urea;
N-[4-(6-hydroxy-2-(4-hydroxyphenyl)naphth-1-ylmethyl)-phenylmethyl]-N'-3-chloro-2-methylphenyl urea;
N-[4-(2-(6-hydroxy-2-(4-hydroxyphenyl)naphth-1-ylmethyl)-phenyl)ethyl]-N'-4-methylphenyl urea;
N-[4-(2-(6-hydroxy-2-(4-hydroxyphenyl)naphth-1-ylmethyl)-phenyl)ethyl]-N'-4-chlorophenyl urea;
N-[4-(2-(6-hydroxy-2-(4-hydroxyphenyl)naphth-1-ylmethyl)-phenyl)ethyl]-N'-4-hydroxyphenyl urea;
N-[4-(2-(6-hydroxy-2-(4-hydroxyphenyl)naphth-1-ylmethyl)-phenyl)ethyl]-N'-4-methoxyphenyl urea;
N-[4-(2-(6-hydroxy-2-(4-hydroxyphenyl)naphth-1-ylmethyl)-phenyl)ethyl]-N'-3-chloro-2-methylphenyl urea;
N-[4-(3-(6-hydroxy-2-(4-hydroxyphenyl)naphth-1-ylmethyl)-phenylpropyl]-N'-4-methylphenyl urea;
N-[4-(3-(6-hydroxy-2-(4-hydroxyphenyl)naphth-1-ylmethyl)-phenylpropyl]-N'-phenyl urea;
N-[4-(3-(6-hydroxy-2-(4-hydroxyphenyl)naphth-1-ylmethyl)-phenylpropyl]-N'-4-chlorophenyl urea;
N-[4-(3-(6-hydroxy-2-(4-hydroxyphenyl)naphth-1-ylmethyl)-phenylpropyl]-N'-4-hydroxyphenyl urea;
N-[4-(3-(6-hydroxy-2-(4-hydroxyphenyl)naphth-1-ylmethyl)-phenylpropyl]-N'-4-methoxyphenyl urea; and
N-[4-(3-(6-hydroxy-2-(4-hydroxyphenyl)naphth-1-ylmethyl)-phenylpropyl]-N'-3-chloro-2-methylphenyl urea.

Compounds of the present invention where Z is N-alkylureido and Z is phenyl or substituted phenyl include:

N-methyl-N-[4-(6-hydroxy-2-(4-hydroxyphenyl)naphth-1-ylmethyl)phenylmethyl]-N'-phenyl urea;
N-methyl-N-[4-(2-(6-hydroxy-2-(4-hydroxyphenyl)naphth-1-ylmethyl)phenyl)ethyl]-N'-phenyl urea;
N-methyl-N-[4-(3-(6-hydroxy-2-(4-hydroxyphenyl)naphth-1-ylmethyl)phenylpropyl]-N'-phenyl urea;
N-methyl-N-[4-(6-hydroxy-2-(4-hydroxyphenyl)naphth-1-ylmethyl)phenylmethyl]-N'-4-methylphenyl urea;
N-methyl-N-[4-(6-hydroxy-2-(4-hydroxyphenyl)naphth-1-ylmethyl)phenylmethyl]-N'-4-chlorophenyl urea;
N-methyl-N-[4-(6-hydroxy-2-(4-hydroxyphenyl)naphth-1-ylmethyl)phenylmethyl]-N'-4-hydroxyphenyl urea;
N-methyl-N-[4-(6-hydroxy-2-(4-hydroxyphenyl)naphth-1-ylmethyl)phenylmethyl]-N'-4-methoxyphenyl urea;
N-methyl-N-[4-(6-hydroxy-2-(4-hydroxyphenyl)naphth-1-ylmethyl)phenylmethyl]-N'-3-chloro-2-methylphenyl urea;
N-methyl-N-[4-(2-(6-hydroxy-2-(4-hydroxyphenyl)naphth-1-ylmethyl)phenyl)ethyl]-N'-4-methylphenyl urea;
N-methyl-N-[4-(2-(6-hydroxy-2-(4-hydroxyphenyl)naphth-1-ylmethyl)phenyl)ethyl]-N'-4-chlorophenyl urea;
N-methyl-N-[4-(2-(6-hydroxy-2-(4-hydroxyphenyl)naphth-1-ylmethyl)phenyl)ethyl]-N'-4-hydroxyphenyl urea;
N-methyl-N-[4-(2-(6-hydroxy-2-(4-hydroxyphenyl)naphth-1-ylmethyl)phenyl)ethyl]-N'-4-methoxyphenyl urea; .
N-methyl-N-[4-(2-(6-hydroxy-2-(4-hydroxyphenyl)naphth-1-ylmethyl)phenyl)ethyl]-N'-3-chloro-2-methylphenyl urea;
N-methyl-N-[4-(3-(6-hydroxy-2-(4-hydroxyphenyl)naphth-1-ylmethyl)phenylpropyl]-N'-4-methylphenyl urea;
N-methyl-N-[4-(3-(6-hydroxy-2-(4-hydroxyphenyl)naphth-1-ylmethyl)phenylpropyl]-N'-phenyl urea;
N-methyl-N-[4-(3-(6-hydroxy-2-(4-hydroxyphenyl)naphth-1-ylmethyl)phenylpropyl]-N'-4-chlorophenyl urea;

N-methyl-N-[4-(3-(6-hydroxy-2-(4-hydroxyphenyl)naphth-1-ylmethyl)phenylpropyl]-N'-4-hydroxyphenyl urea;
N-methyl-N-[4-(3-(6-hydroxy-2-(4-hydroxyphenyl)naphth-1-ylmethyl)phenylpropyl]-N'-4-methoxyphenyl urea;
N-methyl-N-[4-(3-(6-hydroxy-2-(4-hydroxyphenyl)naphth-1-ylmethyl)phenylpropyl]-N'-3-chloro-2-methylphenyl urea;
N-ethyl-N-[4-(6-hydroxy-2-(4-hydroxyphenyl)naphth-1-ylmethyl)phenylmethyl]-N'-4-methylphenyl urea;
N-ethyl-N-[4-(6-hydroxy-2-(4-hydroxyphenyl)naphth-1-ylmethyl)phenylmethyl]-N'-4-chlorophenyl urea;
N-ethyl-N-[4-(6-hydroxy-2-(4-hydroxyphenyl)naphth-1-ylmethyl)phenylmethyl]-N'-4-hydroxyphenyl urea;
N-ethyl-N-[4-(6-hydroxy-2-(4-hydroxyphenyl)naphth-1-ylmethyl)phenylmethyl]-N'-4-methoxyphenyl urea;
N-ethyl-N-[4-(6-hydroxy-2-(4-hydroxyphenyl)naphth-1-ylmethyl)phenylmethyl]-N'-3-chloro-2-methylphenyl urea;
N-ethyl-N-[4-(2-(6-hydroxy-2-(4-hydroxyphenyl)naphth-1-ylmethyl)phenyl)ethyl]-N'-4-methylphenyl urea;
N-ethyl-N-[4-(2-(6-hydroxy-2-(4-hydroxyphenyl)naphth-1-ylmethyl)phenyl)ethyl]-N'-4-chlorophenyl urea;
N-ethyl-N-[4-(2-(6-hydroxy-2-(4-hydroxyphenyl)naphth-1-ylmethyl)phenyl)ethyl]-N'-4-hydroxyphenyl urea;
N-ethyl-N-[4-(2-(6-hydroxy-2-(4-hydroxyphenyl)naphth-1-ylmethyl)phenyl)ethyl]-N'-4-methoxyphenyl urea;
N-ethyl-N-[4-(2-(6-hydroxy-2-(4-hydroxyphenyl)naphth-1-ylmethyl)phenyl)ethyl]-N'-3-chloro-2-methylphenyl urea;
N-ethyl-N-[4-(3-(6-hydroxy-2-(4-hydroxyphenyl)naphth-1-ylmethyl)phenylpropyl]-N'-4-methylphenyl urea;
N-ethyl-N-[4-(3-(6-hydroxy-2-(4-hydroxyphenyl)naphth-1-ylmethyl)phenylpropyl]-N'-phenyl urea;
N-ethyl-N-[4-(3-(6-hydroxy-2-(4-hydroxyphenyl)naphth-1-ylmethyl)phenylpropyl]-N'-4-chlorophenyl urea;
N-ethyl-N-[4-(3-(6-hydroxy-2-(4-hydroxyphenyl)naphth-1-ylmethyl)phenylpropyl]-N'-4-hydroxyphenyl urea;
N-ethyl-N-[4-(3-(6-hydroxy-2-(4-hydroxyphenyl)naphth-1-ylmethyl)phenylpropyl]-N'-4-methoxyphenyl urea; and
N-ethyl-N-[4-(3-(6-hydroxy-2-(4-hydroxyphenyl)naphth-1-ylmethyl)phenylpropyl]-N'-3-chloro-2-methylphenyl urea.

Examples of compounds of the present invention where Y is N'-alkylureido and Z is phenyl or substituted phenyl include:

N-[4-(6-hydroxy-2-(4-hydroxyphenyl)naphth-1-ylmethyl)-phenylmethyl]-N'-methyl-N'-phenyl urea;
N-[4-(2-(6-hydroxy-2-(4-hydroxyphenyl)naphth-1-ylmethyl)-phenyl)ethyl]-N'-methyl-N'-phenyl urea;
N-[4-(3-(6-hydroxy-2-(4-hydroxyphenyl)naphth-1-ylmethyl)-phenylpropyl]-N'-ethyl-N'-phenyl urea;
N-[4-(6-hydroxy-2-(4-hydroxyphenyl)naphth-1-ylmethyl)-phenylmethyl]-N'-methyl-N'-4-methylphenyl urea;
N-[4-(6-hydroxy-2-(4-hydroxyphenyl)naphth-1-ylmethyl)-phenylmethyl]-N'-methyl-N'-4-chlorophenyl urea;
N-[4-(6-hydroxy-2-(4-hydroxyphenyl)naphth-1-ylmethyl)-phenylmethyl]-N'-methyl-N'-4-hydroxyphenyl urea;
N-[4-(6-hydroxy-2-(4-hydroxyphenyl)naphth-1-ylmethyl)-phenylmethyl]-N'-methyl-N'-4-methoxyphenyl urea;
N-[4-(6-hydroxy-2-(4-hydroxyphenyl)naphth-1-ylmethyl)-phenylmethyl]-N'-methyl-N'-3-chloro-2-methylphenyl urea;
N-[4-(6-hydroxy-2-(4-hydroxyphenyl)naphth-1-ylmethyl)-phenylmethyl]-N'-ethyl-N'-4-methylphenyl urea;
N-[4-(6-hydroxy-2-(4-hydroxyphenyl)naphth-1-ylmethyl)-phenylmethyl]-N'-ethyl-N'-4-chlorophenyl urea;
N-[4-(6-hydroxy-2-(4-hydroxyphenyl)naphth-1-ylmethyl)-phenylmethyl]-N'-ethyl-N'-4-hydroxyphenyl urea;
N-[4-(6-hydroxy-2-(4-hydroxyphenyl)naphth-1-ylmethyl)-phenylmethyl]-N'-ethyl-N'-4-methoxyphenyl urea;
N-[4-(6-hydroxy-2-(4-hydroxyphenyl)naphth-1-ylmethyl)-phenylmethyl]-N'-ethyl-N'-3-chloro-2-methylphenyl urea;
N-[4-(2-(6-hydroxy-2-(4-hydroxyphenyl)naphth-1-ylmethyl)-phenyl)ethyl]-N'-methyl-N'-4-methylphenyl urea;
N-[4-(2-(6-hydroxy-2-(4-hydroxyphenyl)naphth-1-ylmethyl)-phenyl)ethyl]-N'-methyl-N'-4-chlorophenyl urea;
N-[4-(2-(6-hydroxy-2-(4-hydroxyphenyl)naphth-1-ylmethyl)-phenyl)ethyl]-N'-methyl-N'-4-hydroxyphenyl urea;
N-[4-(2-(6-hydroxy-2-(4-hydroxyphenyl)naphth-1-ylmethyl)-phenyl)ethyl]-N'-methyl-N'-4-methoxyphenyl urea;
N-[4-(2-(6-hydroxy-2-(4-hydroxyphenyl)naphth-1-ylmethyl)-phenyl)ethyl]-N'-methyl-N'-3-chloro-2-methylphenyl urea;
N-[4-(3-(6-hydroxy-2-(4-hydroxyphenyl)naphth-1-ylmethyl)-phenylpropyl]-N'-ethyl-N'-4-methylphenyl urea;
N-[4-(3-(6-hydroxy-2-(4-hydroxyphenyl)naphth-1-ylmethyl)-phenylpropyl]-N'-ethyl-N'-phenyl urea;
N-[4-(3-(6-hydroxy-2-(4-hydroxyphenyl)naphth-1-ylmethyl)-phenylpropyl]-N'-ethyl-N'-4-chlorophenyl urea;
N-[4-(3-(6-hydroxy-2-(4-hydroxyphenyl)naphth-1-ylmethyl)-phenylpropyl]-N'ethyl-N'-4-hydroxyphenyl urea;
N-[4-(3-(6-hydroxy-2-(4-hydroxyphenyl)naphth-1-ylmethyl)-phenylpropyl]-N'-ethyl-N-4-methoxyphenyl urea; and
N-[4-(3-(6-hydroxy-2-(4-hydroxyphenyl)naphth-1-ylmethyl)-phenylpropyl]-N'-ethyl-N'-3-chloro-2-methylphenyl urea.

The compounds of the present invention are synthesized by standard methods known to practitioners of the organic chemical arts using starting materials which are either commercially available or are prepared by methods disclosed in the chemical literature.

In the present invention, the compounds were prepared by methods of parallel combinatorial synthesis using the process depicted in Reaction Scheme 1. Thus, in each Example presented below, only small amounts of each compound were prepared for purposes of pharmacological evaluation. It will be understood by chemists skilled in the organic chemical art that, if required, larger quantities of each compound disclosed within this specification can be made using the reactions and reagents taught for the combinatorial processes disclosed.

Referring to Reaction Scheme 1, the starting material for the process, [3,4-dihydro-6-methoxy-2-(4-methoxyphenyl)-1-naphthalenyl](4-hydroxyphenyl)methanone, 2, is prepared according to the method disclosed by Jones, et al., *J. Med. Chem.*, 35: 931–938 (1992). The free alcohol function of compound 2 is converted to the triisopropylsiloxyl residue of compound 3 by reaction of 2 with triisopropylsiloxyl triflate (Aldrich Chemical Co., Milwaukee, Wis., USA). The reaction is generally carried out by the method of E. J. Corey, et al., *Tetrahedron Lett.*, 22: 3455 (1981) in dichloromethane in the presence of an acid scavenger such as diisopropylethylamine. The methoxy groups of compound 3 are next removed by reaction of 3 with aluminum chloride and ethanethiol using the method of Node, et al, *Chem. Lett.,* 97 (1979). Subsequent reaction of 3 with lithium aluminum hydride reduces the linking carbonyl group and concomitantly aromatizes the tetrahydronaphthyl ring system of 3 to the naphthyl ring system of 4 after acid treatment.

Compound 4 is next reacted with methoxymethyl chloride (MOM-Cl) using the methods disclosed by G. Stork, et al., *J. Am. Chem. Soc.,* 99: 1275 (1977). This process produces a mixture of isomers 5a and 5b which are carried forward without separation.

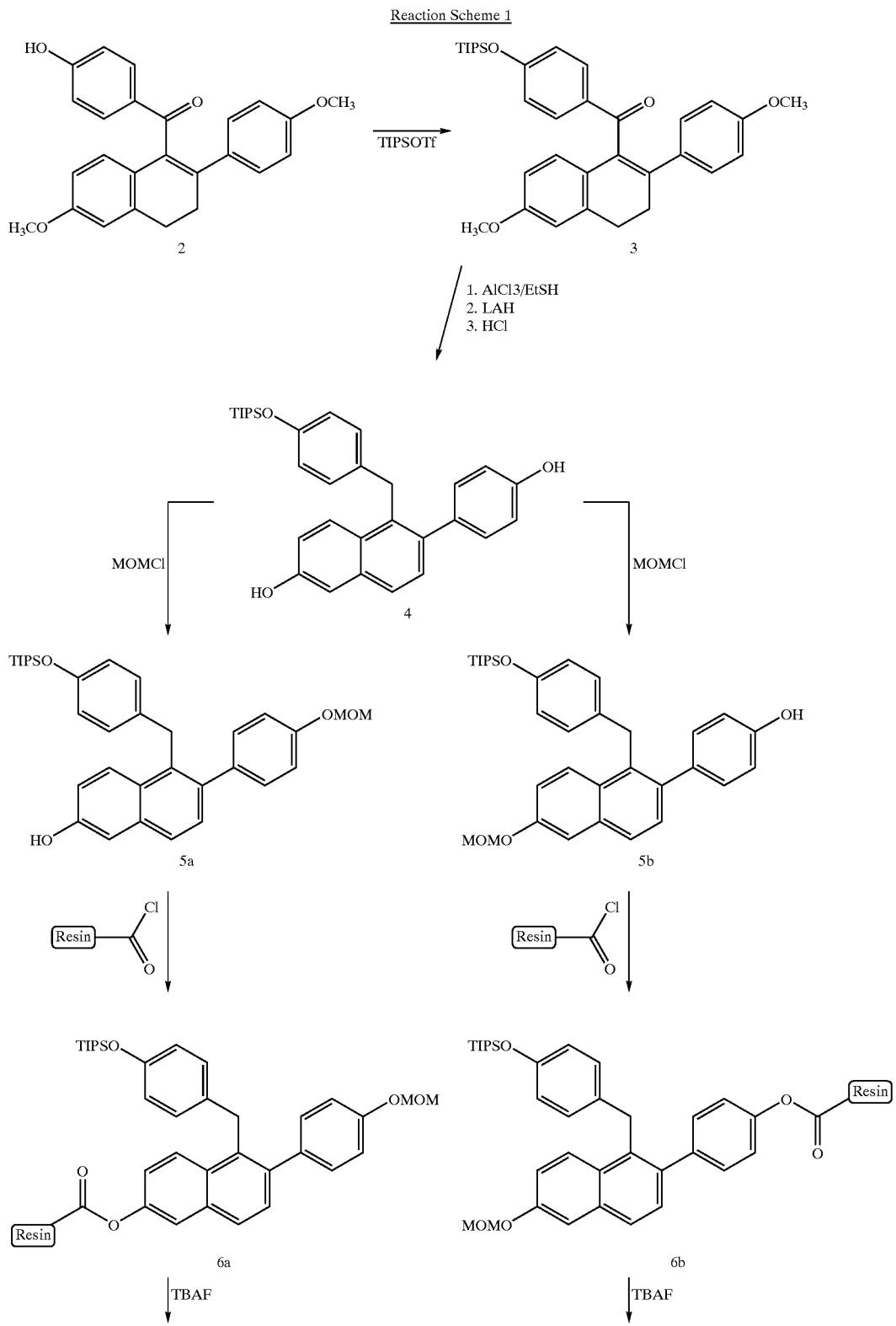

Reaction Scheme 1

-continued
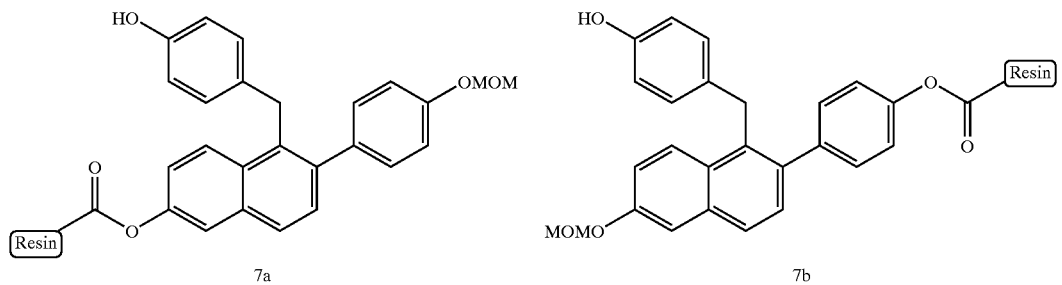
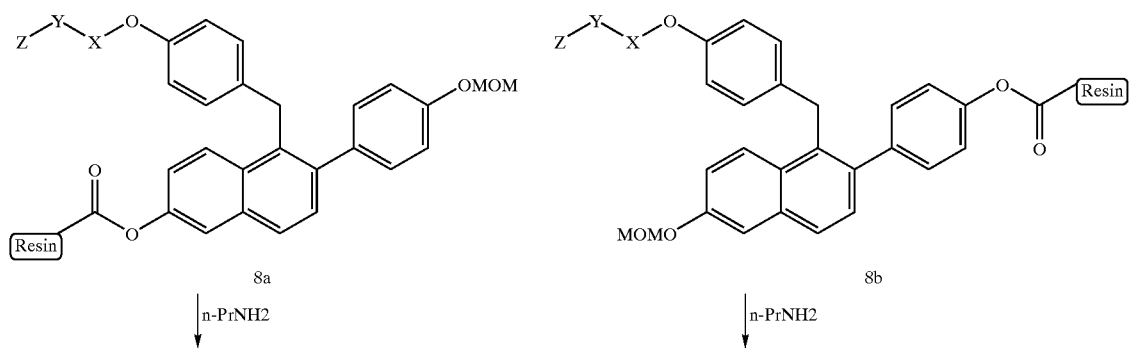
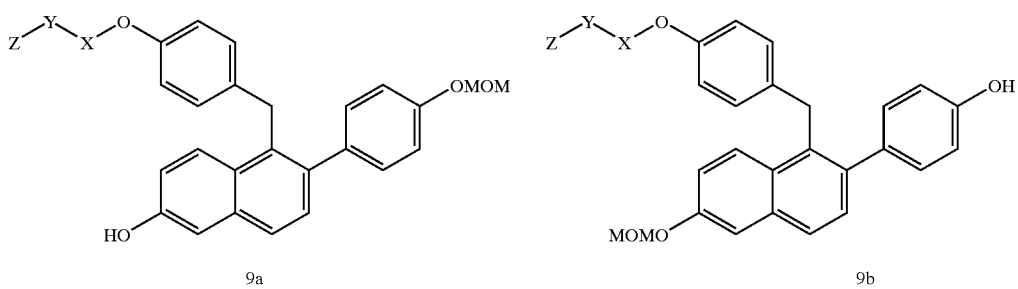
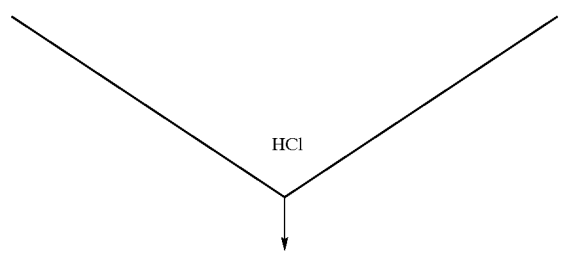

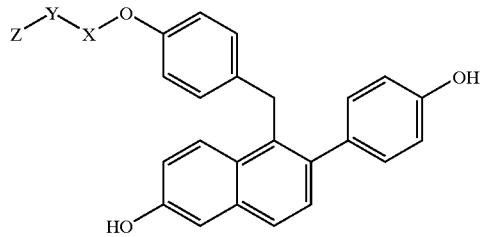

1a

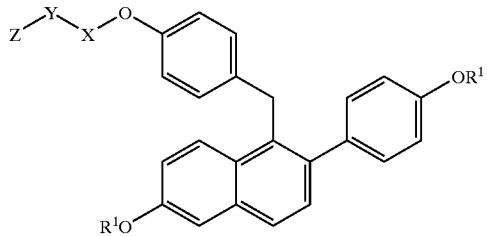

1b

The mixture of isomers, 5a and 5b are next reacted with the acid chloride form of the resin to attach the both triisopropylsilyl protected isomers to the resin backbone. This process is carried out in an aprotic organic solvent, such as dichloromethane, by reacting the acid chloride form of the resin with the protected alcohol mixture in the presence of an amine acid scavenger such as triethylamine. The reaction is typically carried out by gently stirring the mixture (to avoid mechanical breakage of the resin beads) at room temperature for a period of from 8 to 24 hours. The loaded resin, 6a and 6b is then collected by filtration and washed free of the unreacted substrate.

Deprotection of the mixture, 6a and 6b with tetra-n-butylammonium fluoride in tetrahydrofuran, using the method of S. V. Frye, *Tetrahedron Lett.*, 27: 3223 (1986) removes the triisopropylsilyl protecting group and yields the mixture of resin-bound, deprotected isomers 7a and 7b.

The mixture of resin-bound intermediates, 7a and 7b, is next derivatized at the free hydroxyl position by reaction of the free phenolic functions of 7a and 7b with a commercially available alcohol, ZYX—OH, under Mitsunobu conditions (see J. L. Castro, et al., *J. Org. Chem.*, 59: 2289–2291 (1994). These couplings were carried out by combinatorial chemistry means by placing 30 mg (0.04 mmol of the mixture of resin-bound phenolic substrates 7a and 7b in each well of a 96-well plate, together with 0.4 mL of a 1 molar solution of the particular alcohol in toluene. To each well was also added 0.4 mL of a 1 molar suspension of a betaine coupling reagent having the structure

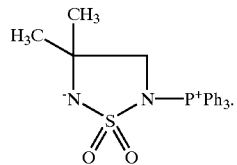

The derivatized, resin-bound mixture of intermediates 8a and 8b are then subjected to cleavage by reaction with n-propylamine at room temperature for a period of about 24 hours to produce the methoxymethyl protected compound mixture 9a and 9b.

In the instances where the desired end-product is a 6-hydroxy-2-(4-hydroxyphenyl)naphthalene of structure 1a where both $R^1$ and $R^2$ are hydrogen, the methoxymethyl protecting groups of 9a and 9b are removed by reaction with acid, typically a trace of 4 molar hydrochloric acid in dioxane, according to the method of J. Auerbach, et al., *J. Chem. Soc., Chem. Commun.*, 298 (1974).

The compounds of structure 1b in which the groups designated $R^1$ are both the same can be prepared directly from 1a by ether-forming or esterification reactions well known in the art.

Referring to Reaction Scheme 2, in the instance where the desired end product of the reaction is a compound of structure 1e in which $R^1$ is alkyl, alkylcarbonyl, or phenylcarbonyl, compound mixture 9a and 9b is first separated by conventional means such as column chromatography. Compound 9a is then reacted under basic conditions to produce the desired methoxymethyl protected ether or ester, 1c, followed by cleavage of the methoxymethyl protecting group to yield the desired product, 1e.

In a similar fashion, if the desired end-product is a compound of structure 1f where $R^2$ is is alkyl, alkylcarbonyl, or phenylcarbonyl, compound 9b (separated from its isomer) is reacted under basic conditions to produce the desired methoxymethyl protected ether or ester, 1c, followed by cleavage of the methoxymethyl protecting group to yield the desired product, 1f.

Specifically, when is it desired that $R^1$ be alkyl, compound 9 is reacted with a suitable base such as potassium Reaction Scheme 2

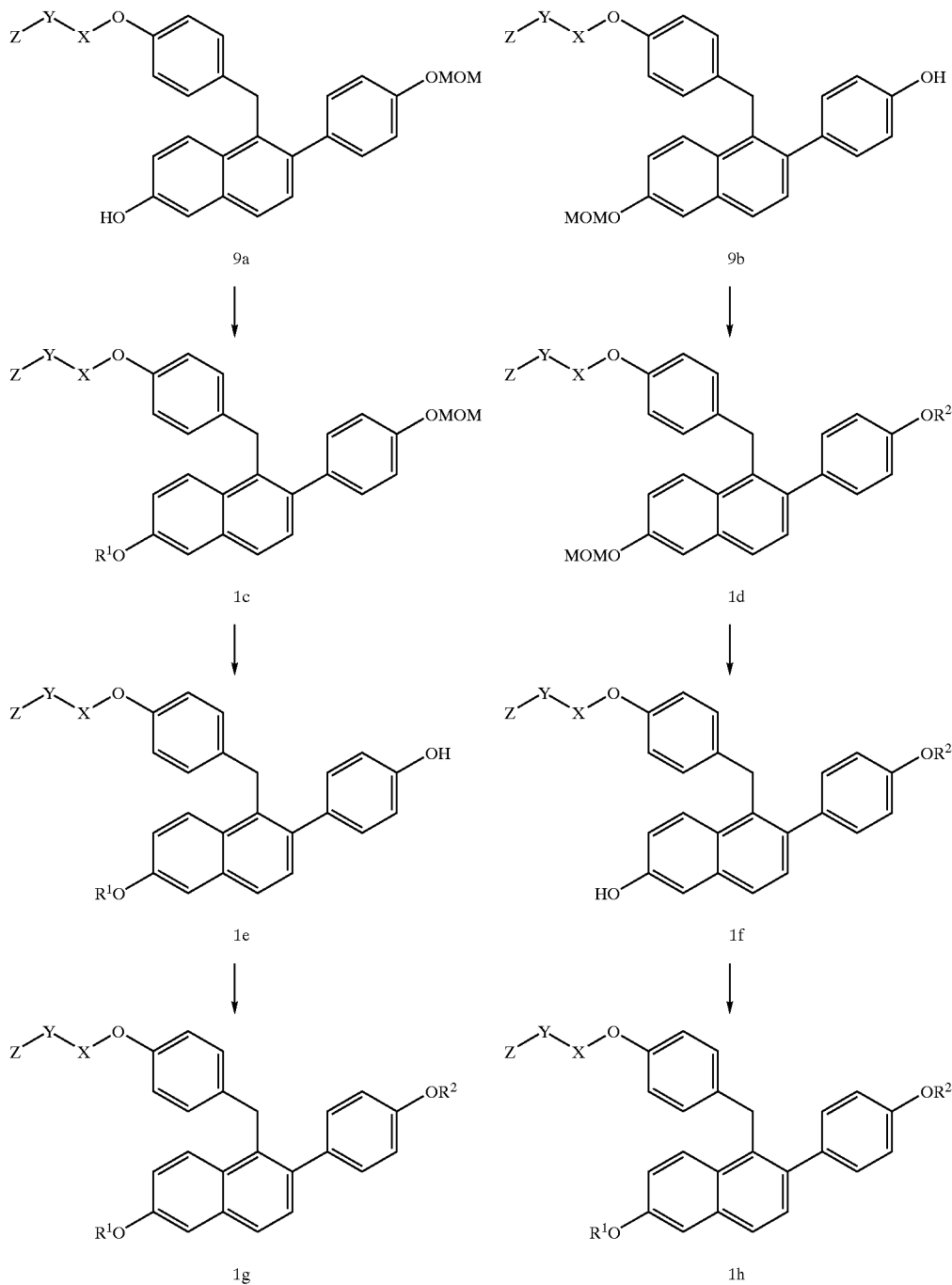

carbonate to yield the corresponding phenolate which is then reacted under typical Williamson ether synthesis conditions with an alkyl chloride to produce the alkyl ether, 1b. In a similar manner, when it is desired that $R^1$ be alkoxycarbonyl, the base-generated phenolate of 9 is reacted with the desired acid chloride in the presence of an acid scavenger such as triethylamine to produce 1b. In those instances where $R^1$ and $R^2$ are the same in the desired end-product, the diethers or diesters are prepared by conventional means from compound 1a (cf. Reaction Scheme 1).

If, in the desired end-product, $R^1$ and $R^2$ are different and other than hydrogen, the free hydroxyl functions of intermediates 1a or 1f are converted by convention means to the desired ether, acyl, or phenacyl group.

Certain compounds falling within the scope of the present invention possess one or more chiral centers and are thus capable of existing in two or more enantiomeric or diastereomeric forms. The present invention contemplates all individual enantiomers of such compounds as well as mixtures thereof in cluding the racemic mixtures.

The individual enantiomers are obtained by methods well known in the art such as the separation by recrystallization of diastereomers formed by reacting racemic mixtures of the enantiomers with a resolved enantiomeric acid. The desired enantiomer is then regenerated from the diastereomeric salt by reaction with base. Alternatively, the individual enantiomers are separated from mixtures by means of standard chromatigraphic separation techniques using "chiral columns," i.e. commercially available chromatographic columns charged with a chiral adsorbant.

The compounds of the present invention in which the substituent Z contains a basic nitrogen atom are capable of forming acid addition salts with a wide variety of organic and inorganic acids and include the physiologically acceptable salts which are often used in the pharmaceutical formulation art. The present invention contemplates within its scope pharmaceutically acceptable acid addition salts of compound of structure 1.

The term "pharmaceutically acceptable salts" denotes salts of the type described by S. M. Berge, et al., *J. Pharm. Sci.*, 66(1): 1–19 (1977) and includes typical inorganic acids such as hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used.

Such pharmaceutically acceptable salts include the acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, hydrobromide, isobutyrate, phenylbutyrate, β-hydroxybutyrate, butyne-1,4-dioate, hexyne-1,4-dioate, caprate, caprylate, hydrochloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxy-ethanesulfonate, methanesulfonate, naphthalene-1-sulfonate, naphthalene-2-sulfonate, p-toluenesulfonate, xylenesulfonate, tartarate, salts and the like.

A preferred salt of compounds of the present invention is the hydrochloride salt.

The pharmaceutically acceptable acid addition salts are typically formed by reacting a compound of formula I with one equivalent (or slight excess) of acid. The reactants are generally combined in a mutual solvent such as diethyl ether, methanol, ethanol, or aqueous alcohol. The salt normally precipitates out of solution within about one hour to 10 days and can be isolated by filtration or the solvent can be stripped off by conventional means.

The pharmaceutically acceptable salts generally have enhanced solubility characteristics compared with the compound from which they are derived, and thus are often more amenable to formulation in solution or emulsion formulations.

For administration to a patient, the compounds of the present invention are formulated into a pharmaceutical formulation using standard practices well known in the formulation art. The present invention also provides pharmaceutical compositions which comprise compounds of the present invention formulated together with one or more non-toxic pharmaceutically acceptable carriers and/or excipients.

The formulations may be specially formulated for oral administration in solid or liquid form, for parenteral injection, or for rectal or vaginal administration by means of a suppository.

The pharmaceutical compositions of this invention can be administered to humans and other mammals orally, rectally, intravaginally, parenterally, topically (by means of powders, ointments, creams, or drops), bucally or sublingually, or as an oral or nasal spray. The term "parenteral administration" refers herein to modes of administration which include intravenous, intramuscular, intraperitoneal, instrasternal, subcutaneous, or intraarticular injection or infusion.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension or crystalline or amorphous material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of the compounds of this invention are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, the active component is mixed with at least one inert, pharmaceutically acceptable carrier such as sodium citrate, or dicalcium phosphate, and/or (a) fillers or extenders such as starches, lactose, glucose, mannitol, and silicic acid, (b) binding agents such as carboxymethylcellulose, alginates, gelatin, poly(vinylpyrrolidine), sucrose and acacia, © humectants such as glycerol, (d) disintegrating agents such as agar-agar, calcium carbonate, potato or tapioca starch, alginic acid, silicates and sodium carbonate, (e) solution retarding agents such as paraffin, (f) absorption accelerating agents such as quaternary ammonium compounds, (g) wetting agents such as cetyl alcohol and glycerin monostearate, (h) absorbents such as kaolin and bentonite clay, and (i) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like. Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of the compounds of this invention include solution, emulsions, suspensions, syrups and elixirs. In addition to the active components, liquid formulations may include inert diluents commonly used in the art such as water or other pharmaceutically acceptable solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing one or more compounds of the present invention with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

Compounds of the present invention may also be administered in the form of liposomes. As is know in the art, liposomes are generally derived from phospholipids or other lipid substances. Liposome formulations are formed by mono- or multilamellar hydrated liquid crystals which are dispersed in an aqueous medium. Any non-toxic, pharmaceutically acceptable, and metabolizable lipid capable of forming liposomes can be used. The present compositions in liposome form can contain, in addition to one or more active compounds of the present invention, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

Dosage forms for topical administration of the compounds of the present invention include powders, sprays, ointments, creams, and inhalants. The active ingredient(s) is mixed under sterile conditions with a suitable pharmaceutically acceptable carrier and preservatives, buffers, or propellants as needed. Opthalmic formulations, eye ointments, and solutions are also contemplated as falling within the scope of the present invention.

Actual dosage levels of compounds of the present invention are varied so as to administer an amount of the compound which is effective to bring about the desired therapeutic affect. The dose required for a given patient will vary depending upon the severity of the condition being treated, the age, weight, and sex of the patient, as well as the state of health of the patient. However, it is within the skill of the art to "dose titrate" the patient; that is, to begin administering a dose known to be below the amount required to bring about the desired therapeutic effect and to gradually increase the dose until the desired effect is achieved.

Generally, for the treatment of estrogen-related disorders, compounds of the present invention are administered at dosage levels between about 10 mg/kg of body weight and about 250 mg/kg of body weight per day. If desired, the daily dosage may be divided into multiple doses for purposes of administration, e.g. into two to four doses per day.

The following Examples are provided in order to enable one skilled in the art to practice the present invention. However, the Examples are merely illustrative of the invention and are not to be read as limiting its scope which is defined by the appended claims.

Preparation 1

Preparation of Acid Chloride Form of Carboxypolystyrene Resin

To a suspension of carboxypolystyrene resin (20.0 g, Novabiochem, La Jolla, Calif., 92039) in benzene (200 mL) under nitrogen atmosphere was added dropwise and excess (20.0 mL) of oxalyl chloride. The resulting mixture was heated to 70° C. for 20 hours, then cooled to ambient temperature. Additional benzene (100 mL) was added to the mixture which was stirred for 5 minutes, and the resulting resin allowed to settle. The supernate was removed via cannula. This procedure was repeated 5 times using 200 ml benzene. After the final rinse, the resulting resin was dried under reduced pressure at 30° C. until a constant mass (19.8 g) was obtained. Chlorine analysis showed the resin contained 8.09% Cl which corresponded to a new loading ratio of 2.29 mmol/g.

Preparation 2

Preparation of a Mixture of the Resin-Bound Phenolic Substrates

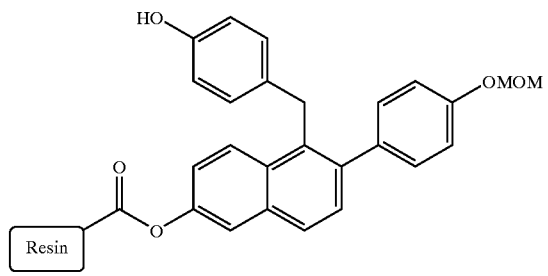

7a and

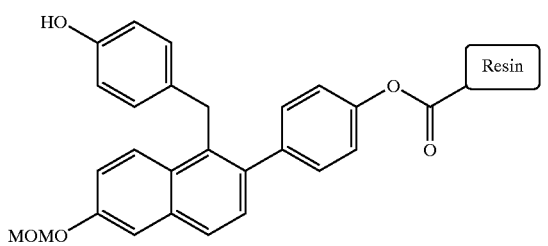

7b

Step 1

Preparation of 6-methoxy-2-(4-methoxyphenyl)-1-(4-triisopropylsilyloxybenzoyl)-3,4-dihydro-naphthalene

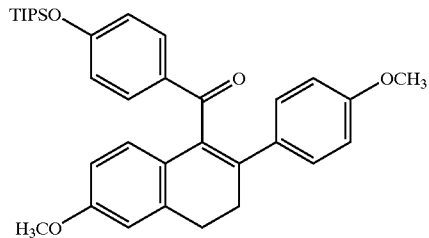

3

To a solution of 5.9 g (15.28 mmol) of 6-methoxy-2-(4-methoxyphenyl)-1-(4-hydroxybenzoyl)-3,4-dihydronaphthalene (prepared as described in Jones, et al., *J. Med. Chem.*, 35: 931–938 (1992) in 200 mL of dichloromethane under a nitrogen atmosphere was added 1.87 g (15.28 mmol) of dimethylamino-pyridine and 4.1 mL (15.28 mmol) of triisopropyl trifluoromethane-sulfonate ("TIPS triflate," Aldrich Chemical Co., Milwaukee, Wis.). The resulting mixture was stirred at room temperature for 48 hours, after which time the reaction was quenched by addition of aqueous sodium bicarbonate solution. The resulting mixture was extracted twice with dichloromethane. The organic layers were combined, extracted with brine solution, dried over anhydrous sodium sulfate and concentrated under vacuum to yield 8.05 g (97%) of the title compound as a thick yellow oil.

$^1$H NMR (300 MHz, CDCl$_3$). δ Values: 1.06 (s, 9H), 1.19 (m, 1H), 2.79 (m, 2H), 3.01 (t, J=7.7, 7.8, 2H), 3.69 (s, 3H), 3.79 (s, 3H), 6.61–6.79 (m, 6H), 6.96 (d, J=8.49, 1H), 7.17 (d, J=6.8, 2H), and 7.73 (d, J=7.13, 2H).

Step 2

Preparation of 6-hydroxy-2-(4-hydroxyphenyl)-1-(4-triisopropylsilyloxybenzyl)naphthalene

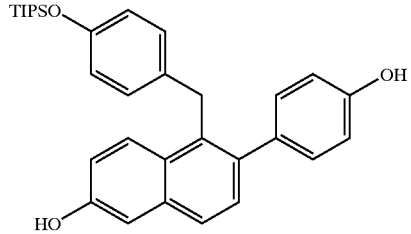

4

To a solution of 8.05 g (14.85 mmol) of the product of step 1 in 200 mL of dichloromethane under a nitrogen atmosphere was added 5.8 mL (78.85 mmol) of ethanethiol followed by 8.41 g (63.08 mmol) of anhydrous aluminum chloride. The resulting mixture was stirred at room temperature for one hour and then cooled to 0° C. The cooled reaction mixture was quickly quenched by the addition of saturated aqueous sodium bicarbonate. Water was added and the mixture was extracted three times with ethyl acetate.

The organic layers were combined, washed with brine, dried over anhydrous sodium sulfate, and concentrated under vacuum to yield 7.2 g of 6-hydroxy-2-(4-hydroxyphenyl)-1-[4-(triisopropylsilyloxy)benzoyl]naphthalene as a yellow solid.

This material was dissolved in 400 mL of tetrahydro-furan under a nitrogen atmosphere and the resulting mixture was cooled to 0° C. Lithium aluminum hydride (42 mL of a 1.0 M solution (42.0 mmol) was added dropwise to the cooled solution with vigorous stirring. This reaction mixture was stirred for 1.5 hours after which time the reaction was quenched by the addition of saturated aqueous sodium bicarbonate. The resulting mixture was extracted three time with ethyl acetate and the organic layers were combine, extracted with brine, dried over anhydrous sodium sulfate, and conentrated under vacuum. The solid residue was taken up in 300 mL of ethyl acetate and a catalytic amount of gaseous hydrogen chloride was bubbled through the solution. The solution was stirred at room temperature for 30 minutes and then quenched with saturated aqueous sodium bicarbonate solution.

This mixture was extracted three times with ethyl acetate, and the organic layers were combines, extrcated with brine, dried over sodium sulfate, and concentrated under vacuum to yield 2.8 g (5.61 mmol, 38%) of the title compound as a yellow foam.

$^1$H NMR (300 MHz, CDCl$_3$). δ Values: 1.06 (s, 9H), 1.19 (m, 1H), 4.31 (s, 2H), 4.71 (s, 1H), 4.99 (s, 1H), 6.72–6.85 (m, 6H), 7.02 (dd, J=6.6, 2.5, 1H), 7.14 (d, J=8.4, 2H), 7.19 (d, J=2.5, 2H), 7.40 (d, J=8.8, 1H), 7.65 (d, ?J=8.5, 1H), and 7.83 (d, J=9.1, 1H).

Step 3

Preparation of mixture of 6-hydroxy-2-(4-methoxy-methoxyphenyl)-1-(4-triisopropylsilyloxybenzoyl)-naphthalene and 6-methoxymethoxy-2-(4-hydroxy-phenyl)-1-(4-triisopropylsilyloxybenzoyl)-naphthalene 5a

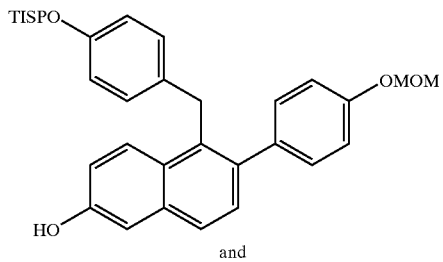

and

5b

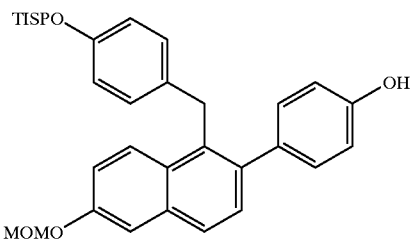

The product of step 2 (2.8 g, 5.61 mmol) was dissolved in 200 mL of acetonitrile under nitrogen at room temperature. To this mixture were 0.78 g (5.61 mmol) of potassium carbonate and a catalytic amount (20 mg) of 1,4,7,10,13,16-hexaoxacyclooctadecane ("18-crown-6" ether, Aldrich Chemical Co., Milwaukee, Wis., USA) and 0.43 mL (5.61 mmol) of methoxymethyl chloride (Aldrich Chemical Co., Milwaukee, Wis., USA). This mixture was stirred at room temperature for 24 hours after which time the reaction was quenched by the addition of saturated sodium bicarbonate.

The reaction mixture was extracted three times with ethyl acetate and the organic layers combined and extracted with brine solution. The organic solution was dried over anhydrous sodium sulfate and concentrated under vacuum. Flash chromatograohy of the resulting oil on silica, eluting with dichloromethane yielded 1.37 g (45%) of a mixture of the two products as a yellow foam.

Step 4

Preparation of mixture of resin-bound 6-hydroxy-2-(4-methoxymethoxyphenyl)-1-(4-triisopropyl-silyloxybenzoyl)naphthalene and 6-methoxymethoxy-2-(4-hydroxyphenyl)-1-(4-triisopropylsilyloxy-benzoyl)naphthalene 6a

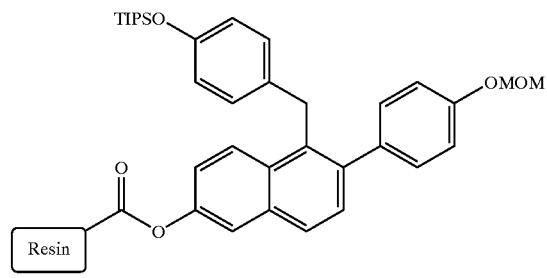

and

6b

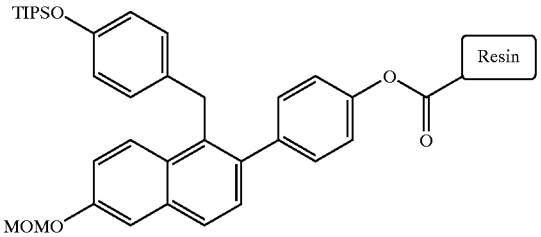

To a solution in 25 mL of dichloromethane of 1.88 g (3.46 mmol) of the product mixture from step 3 were added, under nitrogen, 0.97 mL (6.92 mmol) of triethylamine and 1.51 g (3.46 mmol) of the resin in its acid chloride form (prepared as described in Preparation 1 above). The mixture was stirred gently at room temperature for 19 hours. After this time the reaction was quenched by the addition of 2 mL of methanol and the resulting mixture was stirred at room temperature for an additional 5 minutes. The reaction mixture was filtered and the filter residue was washed successively with 150 mL portions of dichloromethane, methanol, and dichloromethane to yield 2.95 g of the loaded resin with a loading ratio of 1.17 mmol/g.

Step 5

Preparation of the mixture of resin-bound 6-hydroxy-2-(4-methoxymethoxyphenyl)-1-(4-hydroxybenzyl)naphthalene and 6-methoxy-methoxy-2-(4-hydroxyphenyl)-1-(4-hydroxybenzyl)-naphthalene 7a

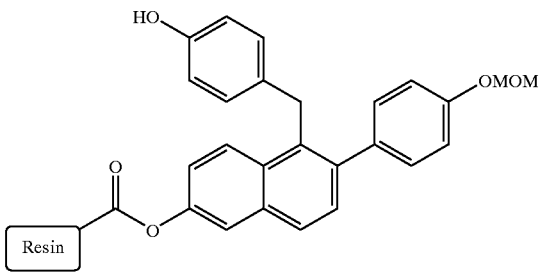

and

7b

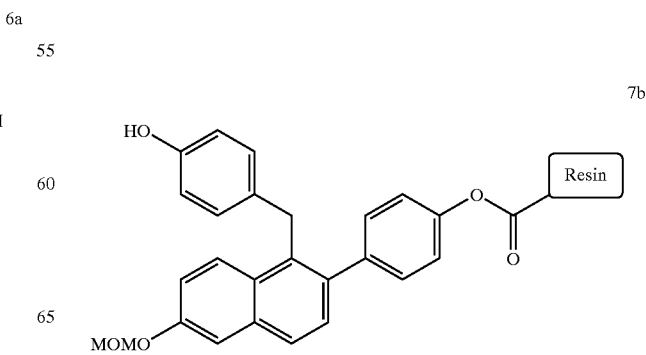

Preparation 3

Preparation of the Betaine Coupling Catalyst

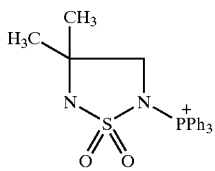

After the method of J. Castro, et al., *J. Org. Chem.*, 59:2289–2291 (1994), to a stirred mixture of triphenylphosphine (8.73 g, 33.28 mmol) and 5.0 g (33.28 mmol) of 3,3-dimethyl-1,2,5-thiazolidine 1.1-dioxide in 100 mL of tetrahydrofuran under nitrogen were added, dropwise over a period of ten minutes, 5.25 mL (33.28 mmol) of diethylazodicarboxylate (DEAD). The resulting mixture was stirred at room temperature for 3 hours and the white solid precipitate which formed was collected by filtration and washed successively once with 20 mL of tetrahydrofuran and twice with 20 mL portions of diethyl ether. The material was dried under high vacuum over phosphorus pentoxide to yield 13.2 g (96%) of the title betaine, m.p. 169–172° C.

General Method for the Preparation of the Compounds of Examples 1–16

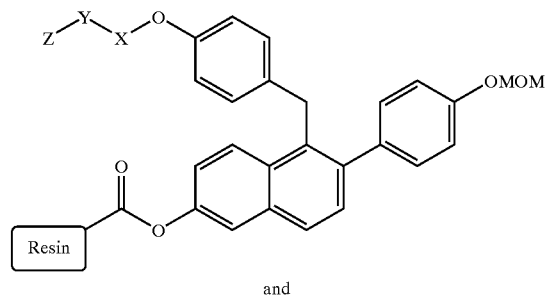

and

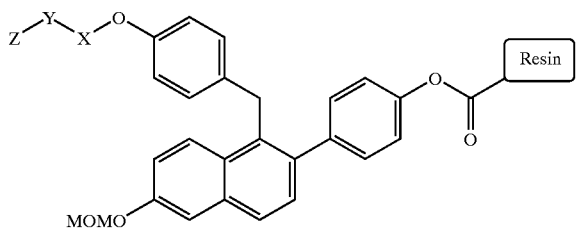

Step 1

Coupling of the Resin-bound and Substrate Alcohols

Reactions were run in a 96-well plate which had been drilled and fitted with filter frits. A mixture of the substrate alcohol (0.4 mL of a 1 molar solution in toluene, 0.04 mmol), 30 mg of the loaded resin beads (0.04 mmol), and 0.4 mmol (0.4 mL of a 1 molar suspension in dichloromethane) were placed in each of well.

The plate was sealed and rotated for 168 hours at room temperature. At the end of this time, each well was filtered through its frit and the residue was washed successively with portions of tetrahydrofuran, dichloro-methane, dimethylformamide, methylene chloride, and tetrahydrofuran.

Step 2

Cleavage of the Derivatized, Methoxymethyl-protected Intermediates from the Resin To each cell was added 0.8 mL of a 20% solution of n-propylamine in tetrahydrofuran. The plated was sealed and vortexed for 24 hours. The contents of each cell were filtered into a normal 96-well plate, collecting each of the cleaved, methoxymethyl-protected intermediates in its own well on the new plate. Each transferred was followed by a rinse of the reaction cells with 15% dichloromethane in methanol.

Step 3

Removal of the Methoxymethyl Protecting Group

To each cell of the new plate containing the cleaved intermediates described in step 2 was added 3.2 mmol of HCl (4 molar in dioxane). The plate was sealed and vortexed overnight. At the end of this time, the solvent and excess HCl were removed under vacuum to yield, in each well of the plate, the end-product of each Example below.

While standard methods of combinatorial chemistry were employed in preparing small amounts of each compound exemplified below, it is within the skill of a practitioner of the organic chemical art to employ the reactions and reagents taught to prepare larger amounts of the compounds if needed.

EXAMPLES 1–16

Each of the Examples below were prepared by the method detailed above. In each case, the molecular weight of the title compound was determined by the ion spray mass spectrometric method and the biological activity determined by the assay described below.

EXAMPLE 1

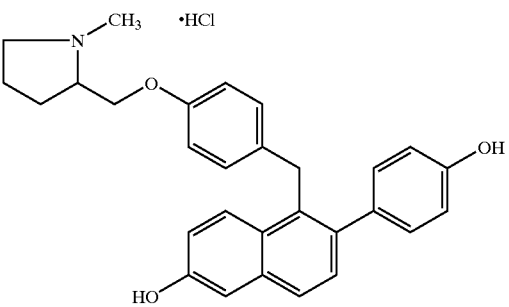

6-Hydroxy-2-(4-hydroxyphenyl)-1-[4-(N-methylpyrrolidin-2-yl)methoxy-benzyl]naphthalene hydrochloride $C_{29}H_{29}NO_3 \cdot HCl$ Mass: (Calc.): 439 (–HCl) (Found): 440

Inhibition of MCF7 cell proliferation: $ED_{50}$=0.5 nM

EXAMPLE 2

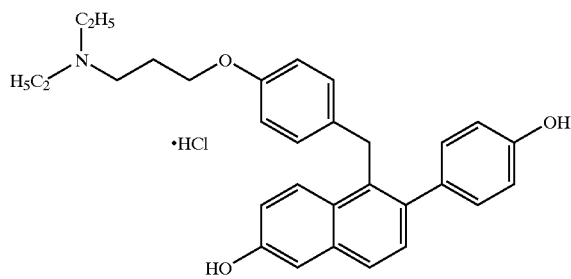

6-Hydroxy-2-(4-hydroxyphenyl)-1-[4-(3-(N,N-diethylamino)-propoxy)benzyl]naphthalene hydrochloride $C_{28}H_{29}NO_3 \cdot HCl$
Mass: (Calc.): 455 (−HCl) (Found): 456
Inhibition of MCF7 cell proliferation: $ED_{50}=0.9$ nM

EXAMPLE 3

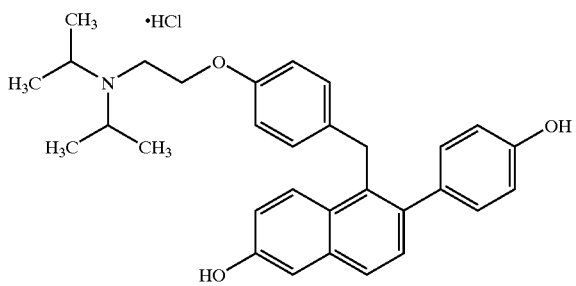

6-hydroxy-2-(4-hydroxyphenyl)-1-[4-(2-(N,N-diisopropyl-amino)ethoxy)benzyl]naphthalene hydrochloride $C_{31}H_{35}NO_3 \cdot HCl$
Mass: (Calc.): 469 (−HCl) (Found): 469
Inhibition of MCF7 cell proliferation: $ED_{50}=2$ nM

EXAMPLE 4

6-hydroxy-2-(4-hydroxyphenyl)-1-[4-(N-methylpiperidin-2-yl)-methoxybenzyl]naphthalene hydrochloride

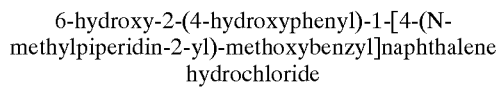

$C_{29}H_{29}NO_3 \cdot HCl$
Mass: (Calc.): 453 (−HCl) (Found): 454
Inhibition of MCF7 cell proliferation: $ED_{50}=2$ nM

EXAMPLE 5

6-hydroxy-2-(4-hydroxyphenyl)-1-[4-(N-methylpiperidin-3-yl)-methoxybenzyl]naphthalene hydrochloride

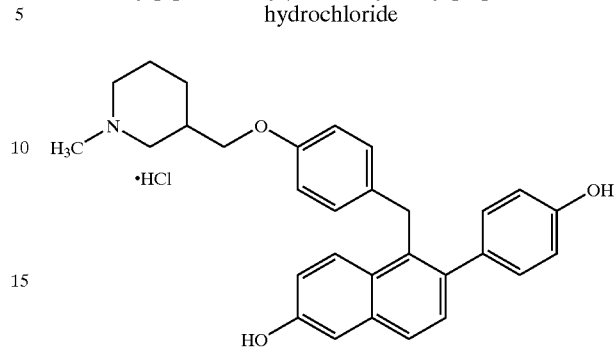

$C_{30}H_{31}NO_3 \cdot HCl$
Mass: (Calc.): 453 (−HCl) (Found): 454
Inhibition of MCF7 cell proliferation: $ED_{50}=2$ nM

EXAMPLE 6

6-hydroxy-2-(4-hydroxyphenyl)-1-[4-(2-(N,N-di-n-butylamino)-ethoxy)benzyl]naphthalene hydrochloride

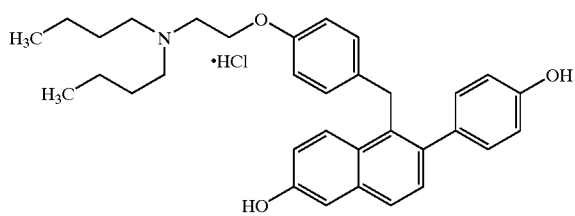

$C_{33}H_{39}NO_3 \cdot HCl$
Mass: (Calc.): 497 (−HCl) (Found): 498
Inhibition of MCF7 cell proliferation: $ED_{50}=2$ nM

EXAMPLE 7

6-hydroxy-2-(4-hydroxyphenyl)-1-[4-(3-(N,N-di-n-butylamino)-propoxy)benzyl]naphthalene hydrochloride

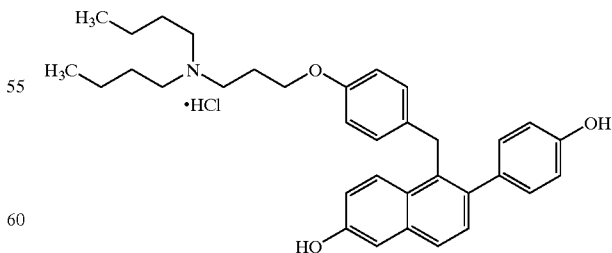

$C_{34}H_{41}NO_3 \cdot HCl$
Mass: (Calc.) : 511 (−HCl) (Found): 512
Inhibition of MCF7 cell proliferation: $ED_{50}=4$ nM

EXAMPLE 8

6-hydroxy-2-(4-hydroxyphenyl)-1-[4-(2-(4-(4-acetylphenyl)piperazin-1-yl)ethoxy)benzyl]-naphthalene dihydrochloride

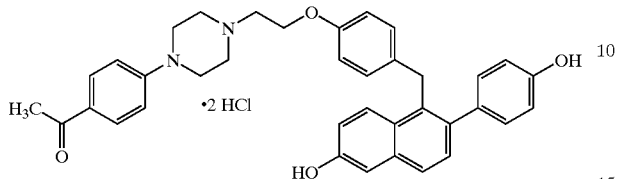

$C_{37}H_{36}N_2O_4 \cdot 2\,HCl$

Mass: (Calc.) : 572 (−2 HCl) (Found): 573

Inhibition of MCF7 cell proliferation: $ED_{50}$=4 nM

EXAMPLE 9

6-hydroxy-2-(4-hydroxyphenyl)-1-[4-(3-(naphth-1-ylamino)propoxy)benzyl]naphthalene hydrochloride

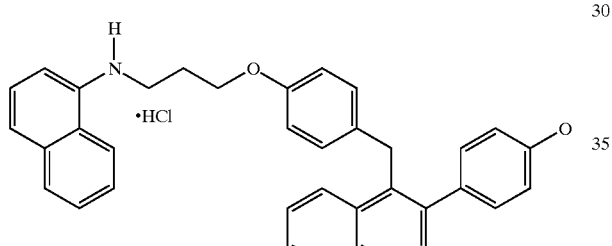

$C_{36}H_{31}NO_3 \cdot HCl$

Mass: (Calc.): 525 (−HCl) (Found): 526

Inhibition of MCF7 cell proliferation: $ED_{50}$=9 nM

EXAMPLE 10

6-hydroxy-2-(4-hydroxyphenyl)-1-[4-(6-(N,N-di-n-butylamino)-hexoxy)benzyl]naphthalene hydrochloride

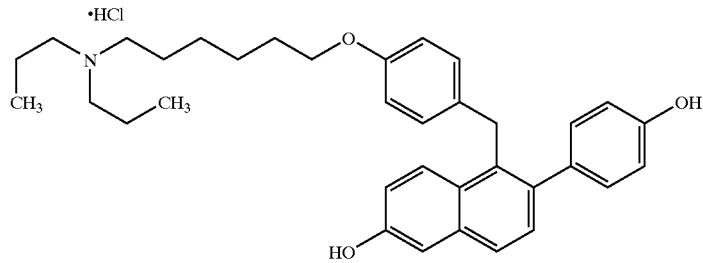

$C_{37}H_{47}NO_3 \cdot HCl$

Mass: (Calc.) : 525 (Found): 526

Inhibition of MCF7 cell proliferation: $ED_{50}$=10 nM

EXAMPLE 11

N-ethyl-N-[4-(2-(6-hydroxy-2-(4-hydroxyphenyl)naphth-1-yl-methyl)phenoxy)ethyl]-N'-5-chloro-2-methylphenyl urea

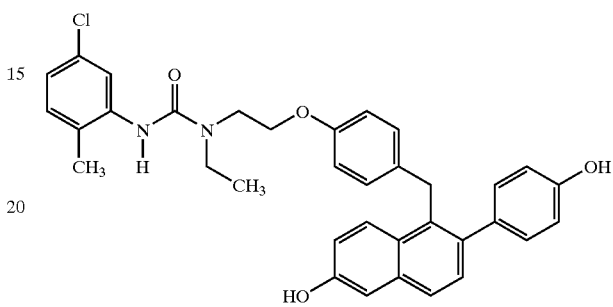

$C_{35}H_{33}ClN_2O_4$

Mass: (Calc.): 580 (Found):

Inhibition of MCF7 cell proliferation: $ED_{50}$=10 nM

EXAMPLE 12

6-hydroxy-2-(4-hydroxyphenyl)-1-[4-(2-(2,3,5,6-tetrahydro-2,6-dioxo-1,3-dimethyl-1H-purin-8-yl)ethoxy)benzyl]naphthalene

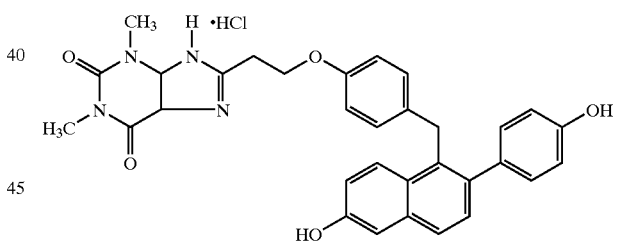

$C_{32}H_{30}N_4O_5$

Mass: (Calc.): 550 (Found): 548

Inhibition of MCF7 cell proliferation: $ED_{50}$=20 nM

EXAMPLE 13

6-hydroxy-2-(4-hydroxyphenyl)-1-[4-(2-(2,6-dimethylmorpholin-4-yl)ethoxy)benzyl]naphthalene hydrochloride

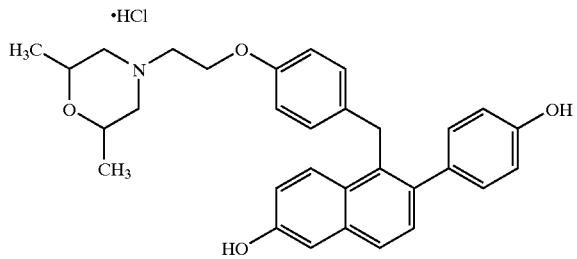

$C_{31}H_{33}NO_4 \cdot HCl$
Mass: (Calc.) : 483 (−HCl) (Found): 483
Inhibition of MCF7 cell proliferation: $ED_{50}=20$ nM

EXAMPLE 14

6-hydroxy-2-(4-hydroxyphenyl)-1-[4-(3-(azaspiro[5.5]undec-4-yl)propoxy)benzyl]naphthalene hydrochloride

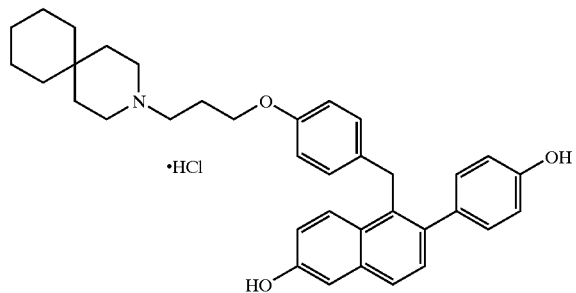

$C_{35}H_{41}NO_3 \cdot HCl$
Mass: (Calc.): 535 (−HCl) (Found): 536
Inhibition of MCF7 cell proliferation: $ED_{50}=30$ nM

EXAMPLE 15

6-hydroxy-2-(4-hydroxyphenyl)-1-[4-(2-(pyrollidinon-1-yl)ethoxy)benzyl]naphthalene

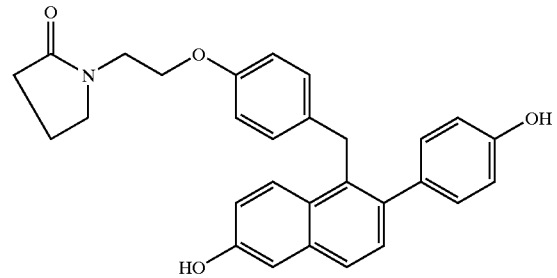

$C_{29}H_{27}NO_4$
Mass: (Calc.): 453 (Found): 454
Inhibition of MCF7 cell proliferation: $ED_{50}=40$ nM

EXAMPLE 16

6-hydroxy-2-(4-hydroxyphenyl)-1-[4-(3-(pyrollidinon-1-yl)propoxy)benzyl]naphthalene

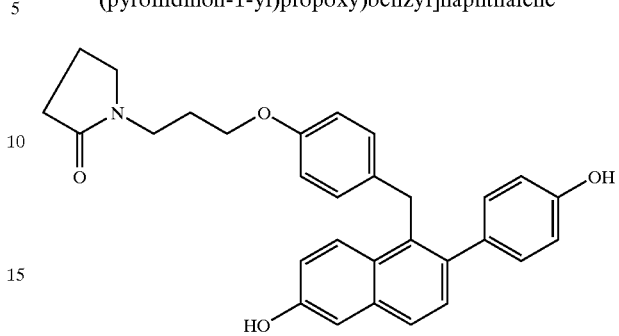

$C_{30}H_{29}NO_4$

Mass: (Calc.): 467 (Found): 468

Inhibition of MCF7 cell proliferation: $ED_{50}=30$ nM

Biological Activity of the Compounds of the Present Invention—MCF-7 Proliferation Assay The data reported in each of the Examples given above for inhibition of MCF-7 cell proliferation were obtained in an assay which determined each compound's ability to inhibit the proliferation of MCF-7 breast adenocarcinoma cells.

In the assay, these cells (ATCC HTB 22) are maintained in minimal essential medium, phenol red-free, (Sigma, St. Louis, Mo.) supplemented with 10% (V/V) fetal bovine serum (FBS), L-glutamine (2 mM), sodium pyruvate (1 mM), HEPES {(N-[2-hydroxyethyl]piperazine-N'-[2-ethanesulfonic acid] 10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 mL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 mL transferred to triplicate microcultures followed by 50 mL assay medium for a final volume of 200 mL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter. Activity of a compound of formula I in this present assay demonstrates that the compound is of potential value for treating hormonally-dependent cancer, particularly breast cancer.

We claim:
1. A compound of the structure:

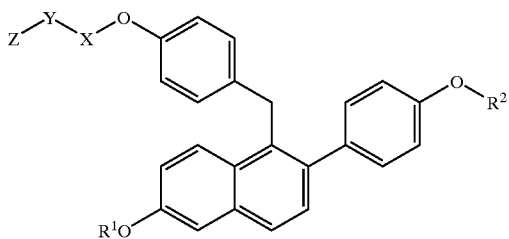

or a pharmaceutically acceptable salt thereof wherein:
$R^1$ and $R^2$ are independently selected from the group consisting of hydrogen, alkyl of one to six carbon atoms, acyl of two to six carbon atoms, and phenacyl;
X is —$(CH_2)_n$ where n is an integer of one to 6, inclusive;
Y is absent or is selected from the group consisting of 1,4-piperazinylene; ureido; N-(lower alkyl)ureido; N'-(lower alkyl)ureido; and N,N'-(di-lower alkyl ureido;
Z is selected from the group consisting of:
1-, 2-, or 3-pyrrolidinyl;
2-, or 3-[1-(lower alkyl)pyrrolidinyl];
1-, 2-, 3-, or 4-piperidinyl;
2-, 3-, or 4-[1-(lower alkyl)piperidinyl];
N-monoalkylamino in which the alkyl group is from one to four carbon atoms;
N,N-dialkylamino in which the alkyl groups are independently from one to four carbon atoms;
1-azepinyl;
1- or 2-naphthylamino;
4-morpholinyl;
dimethyl-4-morpholinyl;
3-azaspiro[5.5]undecan-3-yl;
pyrrolidinonyl-1-yl;
unsubstituted phenyl; and
phenyl substituted with one or two groups independently selected from acyl of two to four carbon atoms, alkyl of one to four carbon atoms, halo, and alkoxy of one to four carbon atoms;
with the proviso that n is 4, 5 or 6 when Z is
1-, 2-, or 3-pyrrolidinyl;
2-, or 3-[1-(lower alkyl)pyrrolidinyl];
1-, 2-, 3-, or 4-piperidinyl;
2-, 3-, or 4-[1-(lower alkyl)piperidinyl];
N,N-dialkylamino in which the alkyl groups are independently from one to four carbon atoms:
1-azepinyl;
4-morpholinyl, or
dimethyl-4-morpholinyl.
2. A compound as defined by claim 1 or a pharmaceutically acceptable salt thereof wherein Y is absent.
3. A compound as defined by claim 2 wherein Z is selected from the group consisting of: 1-pyrrolidinyl, 1-piperidinyl, 1-azepinyl, 4-morpholinyl, dimethyl-4-morpholinyl, and N,N-dialkyl in which the alkyl groups are independently of one to four carbon atoms.
4. A compound as defined by claim 2, or a pharmaceutically acceptable salt thereof, having the name 6-hydroxy-2-(4-hydroxyphenyl)-1-[4-(N-methylamino)-methoxybenzyl]naphthalene;
6-hydroxy-2-(4-hydroxyphenyl)-1-[4-(N-isopropylamino)-methoxybenzyl]naphthalene;
6-hydroxy-2-(4-hydroxyphenyl)-1-[4-(2-N-isopropylamino)ethoxy)benzyl]naphthalene;
6-hydroxy-2-(4-hydroxyphenyl)-1-[4-(3-N-isopropylamino)propoxy)benzyl]naphthalene;
6-hydroxy-2-(4-hydroxyphenyl)-1-[4-(3-N-butylamino)-propoxy)benzyl]naphthalene;
6-hydroxy-2-(4-hydroxyphenyl)-1-[4-(6-(N-methylamino)-hexoxy)benzyl]naphthalene;
6-hydroxy-2-(4-hydroxyphenyl)-1-[4-(6-(N,N-dimethylamino)hexoxy)benzyl]naphthalene;
6-hydroxy-2-(4-hydroxyphenyl)-1-[4-(6-(N-ethylamino)-hexoxy)benzyl]naphthalene;
6-hydroxy-2-(4-hydroxyphenyl)-1-[4-(6-(N,N-diethylamino)hexoxy)benzyl]naphthalene;
6-hydroxy-2-(4-hydroxyphenyl)-1-[4-(6-(N-isopropylamino)hexoxy)benzyl]naphthalene;
6-hydroxy-2-(4-hydroxyphenyl)-1-[4-(6-(N,N-diisopropylamino)hexoxy)benzyl]naphthalene;
6-hydroxy-2-(4-hydroxyphenyl)-1-[4-(6-(N-butylylamino)-hexoxy)benzyl]naphthalene; or
6-hydroxy-2-(4-hydroxyphenyl)-1-[4-(6-(N,N-dibutylamino)hexoxy)benzyl]naphthalene.
5. A compound as defined by claim 2, or a pharmaceutically acceptable salt thereof, having the name 6-hydroxy-2-(4-hydroxyphenyl)-1-[4-(4-(pyrrolidin-1-yl) butoxy)benzyl]naphthalene;
6-hydroxy-2-(4-hydroxyphenyl)-1-[4-(4-(pyrrolidin-2-yl) butoxy)benzyl]naphthalene; or
6-hydroxy-2-(4-hydroxyphenyl)-1-[4-(4-(pyrrolidin-3-yl) butoxy)benzyl]naphthalene.
6. A compound as defined by claim 2, or a pharmaceutically acceptable salt thereof, having the name 6-hydroxy-2-(4-hydroxyphenyl)-1-[4-(4-(piperidin-1-yl)-butoxy)benzyl]naphthalene;
6-hydroxy-2-(4-hydroxyphenyl)-1-[4-(3-(piperidin-2-yl)-butoxy)benzyl]naphthalene;
6-hydroxy-2-(4-hydroxyphenyl)-1-[4-(4-(piperidin-3-yl)-butoxy)benzyl]naphthalene; or
6-hydroxy-2-(4-hydroxyphenyl)-1-[4-(4-(piperidin-4-yl)-butoxy)benzyl]naphthalene.
7. A compound as defined by claim 2 or a pharmaceutically acceptable salt thereof, having the name 6-hydroxy-2-(4-hydroxyphenyl)-1-[4-(azepin-2-yl)-methoxybenzyl]naphthalene;
6-hydroxy-2-(4-hydroxyphenyl)-1-[4-(azepin-3-yl)-methoxybenzyl]naphthalene;
6-hydroxy-2-(4-hydroxyphenyl)-1-[4-(azepin-4-yl)-methoxybenzyl]naphthalene;
6-hydroxy-2-(4-bydroxyphenyl)-1-[4-(2-(azepin-2-yl)-ethoxy)benzyl]naphthalene;
6-hydroxy-2-(4-hydroxyphenyl)-1-[4-(2-(azepin-3-yl)-ethoxy)benzyl]naphthalene;
6-hydroxy-2-(4-hydroxybenzyl)-1-[4-(3-(azepin-2-yl)-propoxy)benzyl]naphthalene;
6-hydroxy-2-(4-hydroxyphenyl)-1-[4-(3-(azepin-3-yl)-propoxy)benzyl]naphthalene;
6-hydroxy-2-(4-hydroxyphenyl)-1-[4-(4-(azepin-1-yl)-butoxy)benzyl]naphthalene;
6-hydroxy-2-(4-hydroxyphenyl)-1-[4-(4-(azepin-2-yl)-butoxy)benzyl]naphthalene;
6-hydroxy-2-(4-hydroxyphenyl)-1-[4-(4-(azepin-3-yl)-butoxy)benzyl]naphthalene; or
6-hydroxy-2-(4-hydroxyphenyl)-1-[4-(4-(azepin-4-yl)-butoxy)benzyl]naphthalene.

37

8. A compound as defined by claim 2 or a pharmaceutically acceptable salt thereof, having the name 6-hydroxy-2-(4-hydroxyphenyl)-1-[4-(4-(morpholin-4-yl)butoxy)benzyl]naphthalene;
6-hydroxy-2-(4-hydroxyphenyl)-1-[4-(5-(morpholin-4-yl)pentoxy)benzyl]naphthalene; or
6-hydroxy-2-(4-hydroxyphenyl)-1-[4-(6-(morpholin-4-yl)hexoxy)benzyl]naphthalene.

9. A compound as defined by claim 2, or a pharmaceutically acceptable salt thereof, selected from the group consisting of 6-hydroxy-2-(4-hydroxyphenyl)-1-[4-(3-azaspiro-[5.5]undec-3-yl)methoxybenzyl]naphthalene;
6-hydroxy-2-(4-hydroxyphenyl)-1-[4-(2-(3-azaspiro-[5.5]undec-3-yl)ethoxy)benzyl]napthalene;
6-hydroxy-2-(4-hydroxyphenyl)-1-[4-(3-(3-azaspiro-[5.5]undec-3-yl)propoxy)benzyl]naphthalene; or
6-hydroxy-2-(4-hydroxyphenyl)-1-[4-(4-(3-azaspiro-[5.5]undec-3-yl)butoxy)benzyl]naphthalene.

10. A compound as defined by claim 2, or a pharmaceutically acceptable salt thereof, having the name 6-hydroxy-2-(4-hydroxyphenyl)-1-[4-(naphth-1-ylamino)-methoxy)benzyl]naphthalene;
6-hydroxy-2-(4-hydroxyphenyl)-1-[4-(2-(naphth-1-ylamino)ethoxy)benzyl]naphthalene;
6-hydroxy-2-(4-hydroxyphenyl)-1-[4-(3-(naphth-1-ylamino)propoxy)benzyl]naphthalene;
6-hydroxy-2-(4-hydroxyphenyl)-1-[4-(4-(naphth-1-ylamino)butoxy)benzyl]naphthalene;
6-hydroxy-2-(4-hydroxyphenyl)-1-[4-(naphth-2-ylamino)-methoxybenzyl]naphthalene;
6-hydroxy-2-(4-hydroxyphenyl)-1-[4-(2-(naphth-2-ylamino)ethoxy)benzyl]naphthalene;
6-hydroxy-2-(4-hydroxyphenyl)-1-[4-(3-(naphth-2-ylamino)propoxy)benzyl]naphthalene; or
6-hydroxy-2-(4-hydroxyphenyl)-1-[4-(4-(naphth-2-ylamino)butoxy)benzyl]naphthalene.

11. A compound as defined by claim 2, or a pharmaceutically acceptable salt thereof, having the name 6-hydroxy-2-(4-hydroxyphenyl)-1-[4-(pyrrolidinon-1-yl)-methoxybenzyl]naphthalene;
6-hydroxy-2-(4-hydroxyphenyl)-1-[4-(2-(pyrrolidinon-1-yl)ethoxy)benzyl]naphthalene;
6-hydroxy-2-(4-hydroxyphenyl)-1-[4-(3-(pyrrolidinon-1-yl)propoxy)benzyl]naphthalene; or
6-hydroxy-2-(4-hydroxyphenyl)-1-[4-(4-(pyrrolidinon-1-yl)butoxy)benzyl]naphthalene.

12. A compound as defined by claim 2, or a pharmaceutically acceptable salt thereof, having the name 6-hydroxy-2-(4-hydroxyphenyl)-1-[4-(2,3,5,6-tetrahydro-2,6-dioxo-1,3-dimethyl-1H-purin-8-yl)methoxybenzyl]naphthalene;
6-hydroxy-2-(4-hydroxyphenyl)-1-[4-(2-(2,3,5,6-tetrahydro-2,6-dioxo-1,3-dimethyl-1H-purin-8-yl)ethoxy)benzyl]naphthalene;
6-hydroxy-2-(4-hydroxyphenyl)-1-[4-(3-(2,3,5,6-tetrahydro-2,6-dioxo-1,3-dimethyl-1H-purin-8-yl)propoxy)benzyl]naphthalene; or
6-hydroxy-2-(4-hydroxyphenyl)-1-[4-(4-(2,3,5,6-tetrahydro-2,6-dioxo-1,3-dimethyl-1H-purin-8-yl)butoxy)benzyl]naphthalene.

13. A compound as defined by claim 1 or a pharmaceutically acceptable salt thereof wherein Z is 1,4-piperazinylene.

14. A compound as defined by claim 14, or a pharmaceutically acceptable salt thereof, having the name 6-hydroxy-2-(4-hydroxyphenyl)-1-[4-(4-phenylpiperazin-1-ylmethoxy)benzyl]naphthalene;
6-hydroxy-2-(4-hydroxyphenyl)-1-[4-(2-(4-phenylpiperazin-1-yl)ethoxy)benzyl]naphthalene;
6-hydroxy-2-(4-hydroxyphenyl)-1-[4-(3-(4-phenylpiperazin-1-yl)propoxy)benzyl]naphthalene;
6-hydroxy-2-(4-hydroxyphenyl)-1-[4-(4-(4-phenyl-piperazin-1-yl)butoxy)benzyl]naphthalene;
6-hydroxy-2-(4-hydroxyphenyl)-1-[4-(4-(4-methyl-phenyl)piperazin-1-ylmethoxy)benzyl]naphthalene;
6-hydroxy-2-(4-hydroxyphenyl)-1-[4-(4-(4-chlorophenyl)piperazin-1-ylmethoxy)benzyl]naphthalene;
6-hydroxy-2-(4-hydroxyphenyl)-1-[4-(4-(4-hydroxyphenyl)piperazin-1-ylmethoxy)benzyl]naphthalene;
6-hydroxy-2-(4-hydroxyphenyl)-1-[4-(4-(4-methoxyphenyl)piperazin-1-ylmethoxy)benzyl]naphthalene;
6-hydroxy-2-(4-hydroxyphenyl)-1-[4-(4-(4-acetylphenyl)piperazin-1-ylmethoxy)benzyl]naphthalene;
6-hydroxy-2-(4-hydroxyphenyl)-1-[4-(2-(4-(4-methylphenyl)piperazin-1-yl)ethoxy)benzyl]naphthalene;
6-hydroxy-2-(4-hydroxyphenyl)-1-[4-(2-(4-(4-chlorophenyl)piperazin-1-yl)ethoxy)benzyl]naphthalene;
6-hydroxy-2-(4-hydroxyphenyl)-1-[4-(2-(4-(4-hydroxyphenyl)piperazin-1-yl)ethoxy)benzyl]naphthalene;
6-hydroxy-2-(4-hydroxyphenyl)-1-[4-(2-(4-(4-methoxyphenyl)piperazin-1-yl)ethoxy)benzyl]naphthalene;
6-hydroxy-2-(4-hydroxyphenyl)-1-[4-(2-(4-(4-acetylphenyl)piperazin-1-yl)ethoxy)benzyl]naphthalene;
6-hydroxy-2-(4-hydroxyphenyl)-1-[4-(3-(4-(4-methylphenyl)piperazin-1-yl)propoxy)benzyl]naphthalene;
6-hydroxy-2-(4-hydroxyphenyl)-1-[4-(3-(4-(4-chlorophenyl)piperazin-1-yl)propoxy)benzyl]naphthalene;
6-hydroxy-2-(4-hydroxyphenyl)-1-[4-(3-(4-(4-hydroxyphenyl)piperazin-1-yl)propoxy)benzyl]naphthalene;
6-hydroxy-2-(4-hydroxyphenyl)-1-[4-(3-(4-(4-methoxyphenyl)piperazin-1-yl)propoxy)benzyl]naphthalene; or 6-hydroxy-2-(4-hydroxyphenyl)-1-[4-(3-(4-(4-acetylphenyl)piperazin-1-yl)propoxy)benzyl]naphthalene.

15. A compound as defined by claim 1 or a pharmaceutically acceptable salt thereof wherein Y is selected from ureido, N-(lower alkyl)ureido, N'-(lower alkyl)ureido, and N,N'-di(lower alkyl)ureido having the name N-[4-(6-hydroxy-2-(4-hydroxyphenyl)naphth-1-ylmethyl)-phenylmethyl]-N'-phenyl urea;
N-[4-(2-(6-hydroxy-2-(4-hydroxyphenyl)naphth-1-ylmethyl)phenyl)ethyl]-N'-phenyl urea;
N-[4-(3-(6-hydroxy-2-(4-hydroxyphenyl)naphth-1-ylmethyl)phenylpropyl]-N'-phenyl urea;
N-[4-(6-hydroxy-2-(4-hydroxyphenyl)naphth-1-ylmethyl)-phenylmethyl]-N'-4-methylphenyl urea;
N-[4-(6-hydroxy-2-(4-hydroxyphenyl)naphth-1-ylmethyl)-phenylmethyl]-N'-4-chlorophenyl urea;
N-[4-(6-hydroxy-2-(4-hydroxyphenyl)naphth-1-ylmethyl)-phenylmethyl]-N'-4-hydroxyphenyl urea;
N-[4-(6-hydroxy-2-(4-hydroxyphenyl)naphth-1-ylmethyl)-phenylmethyl]-N'-4-methoxyphenyl urea;

N-[4-(6-hydroxy-2-(4-hydroxyphenyl)naphth-1-ylmethyl)-phenylmethyl]-N'-3-chloro-2-methylphenyl urea;
N-[4-(2-(6-hydroxy-2-(4-hydroxyphenyl)naphth-1-ylmethyl)phenyl)ethyl]-N'-4-methylphenyl urea;
N-[4-(2-(6-hydroxy-2-(4-hydroxyphenyl)naphth-1-ylmethyl)phenyl)ethyl]-N'-4-chlorophenyl urea;
N-[4-(2-(6-hydroxy-2-(4-hydroxyphenyl)naphth-1-ylmethyl)phenyl)ethyl]-N'-4-hydroxyphenyl urea;
N-[4-(2-(6-hydroxy-2-(4-hydroxyphenyl)naphth-1-ylmethyl)phenyl)ethyl]-N'-4-methoxyphenyl urea;
N-[4-(2-(6-hydroxy-2-(4-hydroxyphenyl)naphth-1-ylmethyl)phenyl)ethyl]-N'-3-chloro-2-methylphenyl urea;
N-[4-(3-(6-hydroxy-2-(4-hydroxyphenyl)naphth-1-ylmethyl)phenylpropyl]-N'-4-methylphenyl urea;
N-[4-(3-(6-hydroxy-2-(4-hydroxyphenyl)naphth-1-ylmethyl)phenylpropyl]-N'-phenyl urea;
N-[4-(3-(6-hydroxy-2-(4-hydroxyphenyl)naphth-1-ylmethyl)phenylpropyl]-N'-4-chlorophenyl urea;
N-[4-(3-(6-hydroxy-2-(4-hydroxyphenyl)naphth-1-ylmethyl)phenylpropyl]-N'-4-hydroxyphenyl urea;
N-[4-(3-(6-hydroxy-2-(4-hydroxyphenyl)naphth-1-ylmethyl)phenylpropyl]-N'-4-methoxyphenyl urea; and
N-[4-(3-(6-hydroxy-2-(4-hydroxyphenyl)naphth-1-ylmethyl)phenylpropyl]-N'-3-chloro-2-methylphenyl urea;
N-methyl-N-[4-(6-hydroxy-2-(4-hydroxyphenyl)naphth-1-ylmethyl)phenylmethyl]-N'-phenyl urea;
N-methyl-N-[4-(2-(6-hydroxy-2-(4-hydroxyphenyl)naphth-1-ylmethyl)phenyl)ethyl]-N'-phenyl urea;
N-methyl-N-[4-(3-(6-hydroxy-2-(4-hydroxyphenyl)naphth-1-ylmethyl)phenylpropyl]-N'-phenyl urea;
N-methyl-N-[4-(6-hydroxy-2-(4-hydroxyphenyl)naphth-1-ylmethyl)phenylmethyl]-N'-4-methylphenyl urea;
N-methyl-N-[4-(6-hydroxy-2-(4-hydroxyphenyl)naphth-1-ylmethyl)phenylmethyl]-N'-4-chlorophenyl urea;
N-methyl-N-[4-(6-hydroxy-2-(4-hydroxyphenyl)naphth-1-ylmethyl)phenylmethyl]-N'-4-hydroxyphenyl urea;
N-methyl-N-[4-(6-hydroxy-2-(4-hydroxyphenyl)naphth-1-ylmethyl)phenylmethyl]-N'-4-methoxyphenyl urea;
N-methyl-N-[4-(6-hydroxy-2-(4-hydroxyphenyl)naphth-1-ylmethyl)phenylmethyl]-N'-3-chloro-2-methylphenyl urea;
N-methyl-N-[4-(2-(6-hydroxy-2-(4-hydroxyphenyl)naphth-1-ylmethyl)phenyl)ethyl]-N'-4-methylphenyl urea;
N-methyl-N-[4-(2-(6-hydroxy-2-(4-hydroxyphenyl)naphth-1-ylmethyl)phenyl)ethyl]-N'-4-chlorophenyl urea;
N-methyl-N-[4-(2-(6-hydroxy-2-(4-hydroxyphenyl)naphth-1-ylmethyl)phenyl)ethyl]-N'-4-hydroxyphenyl urea;
N-methyl-N-[4-(2-(6-hydroxy-2-(4-hydroxyphenyl)naphth-1-ylmethyl)phenyl)ethyl]-N'-4-methoxyphenyl urea;
N-methyl-N-[4-(2-(6-hydroxy-2-(4-hydroxyphenyl)naphth-1ylmethyl)phenyl)ethyl]-N'-3-chloro-2-methylphenyl urea;
N-methyl-N-[4-(3-(6-hydroxy-2-(4-hydroxyphenyl)naphth-1-ylmethyl)phenylpropyl]-N'-4-methylphenyl urea;
N-methyl-N-[4-(3-(6-hydroxy-2-(4-hydroxyphenyl)naphth-1-ylmethyl)phenylpropyl]-N'-phenyl urea;
N-methyl-N-[4-(3-(6-hydroxy-2-(4-hydroxyphenyl)naphth-1-ylmethyl)phenylpropyl]-N'-4-chlorophenyl urea;
N-methyl-N-[4-(3-(6-hydroxy-2-(4-hydroxyphenyl)naphth-1-ylmethyl)phenylpropyl]-N'-4-hydroxyphenyl urea;
N-methyl-N-[4-(3-(6-hydroxy-2-(4-hydroxyphenyl)naphth-1-ylmethyl)phenylpropyl]-N'-4-methoxyphenyl urea;
N-methyl-N-[4-(3-(6-hydroxy-2-(4-hydroxyphenyl)naphth-1-ylmethyl)phenylpropyl]-N'-3-chloro-2-methylphenyl urea;
N-ethyl-N-[4-(6-hydroxy-2-(4-hydroxyphenyl)naphth-1-ylmethyl)phenylmethyl]-N'-4-methylphenyl urea;
N-ethyl-N-[4-(6-hydroxy-2-(4-hydroxyphenyl)naphth-1-ylmethyl)phenylmethyl]-N'-4-chlorophenyl urea;
N-ethyl-N-[4-(6-hydroxy-2-(4-hydroxyphenyl)naphth-1-ylmethyl)phenylmethyl]-N'-4-hydroxyphenyl urea;
N-ethyl-N-[4-(6-hydroxy-2-(4-hydroxyphenyl)naphth-1-ylmethyl)phenylmethyl]-N'-4-methoxyphenyl urea;
N-ethyl-N-[4-(6-hydroxy-2-(4-hydroxyphenyl)naphth-1-ylmethyl)phenylmethyl]-N'-3-chloro-2-methylphenyl urea;
N-ethyl-N-[4-(2-(6-hydroxy-2-(4-hydroxyphenyl)naphth-1-ylmethyl)phenyl)ethyl]-N'-4-methylphenyl urea;
N-ethyl-N-[4-(2-(6-hydroxy-2-(4-hydroxyphenyl)naphth-1-ylmethyl)phenyl)ethyl]-N'-4-chlorophenyl urea;
N-ethyl-N-[4-(2-(6-hydroxy-2-(4-hydroxyphenyl)naphth-1-ylmethyl)phenyl)ethyl]-N'-4-hydroxyphenyl urea;
N-ethyl-N-[4-(2-(6-hydroxy-2-(4-hydroxyphenyl)naphth-1-ylmethyl)phenyl)ethyl]-N'-4-methoxyphenyl urea;
N-ethyl-N-[4-(2-(6-hydroxy-2-(4-hydroxyphenyl)naphth-1-ylmethyl)phenyl)ethyl]-N'-3-chloro-2-methylphenyl urea;
N-ethyl-N-[4-(3-(6-hydroxy-2-(4-hydroxyphenyl)naphth-1-ylmethyl)phenylpropyl]-N'-4-methylphenyl urea;
N-ethyl-N-[4-(3-(6-hydroxy-2-(4-hydroxyphenyl)naphth-1-ylmethyl)phenylpropyl]-N'-phenyl urea;
N-ethyl-N-[4-(3-(6-hydroxy-2-(4-hydroxyphenyl)naphth-1-ylmethyl)phenylpropyl]-N'-4-chlorophenyl urea;
N-ethyl-N-[4-(3-(6-hydroxy-2-(4-hydroxyphenyl)naphth-1-ylmethyl)phenylpropyl]-N'-4-hydroxyphenyl urea;
N-ethyl-N-[4-(3-(6-hydroxy-2-(4-hydroxyphenyl)naphth-1-ylmethyl)phenylpropyl]-N'-4-methoxyphenyl urea;
N-ethyl-N-[4-(3-(6-hydroxy-2-(4-hydroxyphenyl)naphth-1-ylmethyl)phenylpropyl]-N'-3-chloro-2-methylphenyl urea;
N-[4-(6-hydroxy-2-(4-hydroxyphenyl)naphth-1-ylmethyl)-phenylmethyl]-N'-methyl-N'-phenyl urea;
N-[4-(2-(6-hydroxy-2-(4-hydroxyphenyl)naphth-1-ylmethyl)phenyl)ethyl]-N'-methyl-N'-phenyl urea;
N-[4-(3-(6-hydroxy-2-(4-hydroxyphenyl)naphth-1-ylmethyl)phenylpropyl]-N'-ethyl-N'-phenyl urea;
N-[4-(6-hydroxy-2-(4-hydroxyphenyl)naphth-1-ylmethyl)-phenylmethyl]-N'-methyl-N'-4-methylphenyl urea;
N-[4-(6-hydroxy-2-(4-hydroxyphenyl)naphth-1-ylmethyl)-phenylmethyl]-N'-methyl-N'-4-chlorophenyl urea;
N-[4-(6-hydroxy-2-(4-hydroxyphenyl)naphth-1-ylmethyl)-phenylmethyl]-N'-methyl-N'-4-hydroxyphenyl urea;
N-[4-(6-hydroxy-2-(4-hydroxyphenyl)naphth-1-ylmethyl)-phenylmethyl]-N'-methyl-N'-4-methoxyphenyl urea;
N-[4-(6-hydroxy-2-(4-hydroxyphenyl)naphth-1-ylmethyl)-phenylmethyl]-N'-methyl-N'-3-chloro-2-methylphenyl urea;
N-[4-(6-hydroxy-2-(4-hydroxyphenyl)naphth-1-ylmethyl)-phenylmethyl]-N'-ethyl-N'-4-methylphenyl urea;
N-[4-(6-hydroxy-2-(4-hydroxyphenyl)naphth-1-ylmethyl)-phenylmethyl]-N'-ethyl-N'-4-chlorophenyl urea;
N-[4-(6-hydroxy-2-(4-hydroxyphenyl)naphth-1-ylmethyl)-phenylmethyl]-N'-ethyl-N'-4-hydroxyphenyl urea;
N-[4-(6-hydroxy-2-(4-hydroxyphenyl)naphth-1-ylmethyl)-phenylmethyl-N'-ethyl-N'-4-methoxyphenyl urea;
N-[4-(6-hydroxy-2-(4-hydroxyphenyl)naphth-1-ylmethyl)-phenylmethyl]-N'-ethyl-N'-3-chloro-2-methylphenyl urea;
N-[4-(2-(6-hydroxy-2-(4-hydroxyphenyl)naphth-1-ylmethyl)phenyl)ethyl]-N'-methyl-N'-4-methylphenyl urea;
N-[4-(2-(6-hydroxy-2-(4-hydroxyphenyl)naphth-1-ylmethyl)phenyl)ethyl]-N'-methyl-N'-4-chlorophenyl urea;

N-[4-(2-(6-hydroxy-2-(4-hydroxyphenyl)naphth-1-ylmethyl)phenyl)ethyl]-N'-methyl-N'-4-hydroxyphenyl urea;

N-[4-(2-(6-hydroxy-2-(4-hydroxyphenyl)naphth-1-ylmethyl)phenyl)ethyl]-N'-methyl-N'-4-methoxyphenyl urea;

N-[4-(2-(6-hydroxy-2-(4-hydroxyphenyl)naphth-1-ylmethyl)phenyl)ethyl]-N'-methyl-N'-3-chloro-2-methylphenyl urea;

N-[4-(3-(6-hydroxy-2-(4-hydroxyphenyl)naphth-1-ylmethyl)phenylpropyl]-N'-ethyl-N'-4-methylphenyl urea;

N-[4-(3-(6-hydroxy-2-(4-hydroxyphenyl)naphth-1-ylmethyl)phenylpropyl]-N'-ethyl-N'-phenyl urea;

N-[4-(3-(6-hydroxy-2-(4-hydroxyphenyl)naphth-1-ylmethyl)phenylpropyl]-N'-ethyl-N'-4-chlorophenyl urea;

N-[4-(3-(6-hydroxy-2-(4-hydroxyphenyl)naphth-1-ylmethyl)phenylpropyl]-N'ethyl-N'-4-hydroxyphenyl urea;

N-[4-(3-(6-hydroxy-2-(4-hydroxyphenyl)naphth-1-ylmethyl)phenylpropyl]-N'-ethyl-N-4-methoxyphenyl urea; or N-ethyl-N-[4-(2-(6-hydroxy-2-(4-hydroxyphenyl)naphth-1-ylmethyl)phenoxy)ethyl]-N'-5-chloro-2-methylphenyl urea.

16. A pharmaceutical composition comprising a therapeutically effective amount of a compound as defined by claim 1 in combination with a pharmaceutically acceptable carrier.

17. A method for the treatment of breast cancer in a woman comprising administering to a patient a therapeutically effective amount of a compound as defined by claim 1.

* * * * *